(12) United States Patent
Rabbani

(10) Patent No.: US 8,658,380 B2
(45) Date of Patent: Feb. 25, 2014

(54) DIAGNOSTIC AND THERAPEUTIC TARGET

(75) Inventor: Hodjattallah Rabbani, Stockholm (SE)

(73) Assignee: Avicenna Research Institute, Tehran (IR)

( * ) Notice: Subject to any disclaimer, the term of this patent is extended or adjusted under 35 U.S.C. 154(b) by 0 days.

(21) Appl. No.: 13/636,117

(22) PCT Filed: Oct. 28, 2011

(86) PCT No.: PCT/SE2011/051289
§ 371 (c)(1),
(2), (4) Date: Oct. 15, 2012

(87) PCT Pub. No.: WO2012/057697
PCT Pub. Date: May 3, 2012

(65) Prior Publication Data
US 2013/0039917 A1    Feb. 14, 2013

Related U.S. Application Data

(60) Provisional application No. 61/407,556, filed on Oct. 28, 2010.

(30) Foreign Application Priority Data
Nov. 5, 2010    (SE) ...................................... 1051158

(51) Int. Cl.
*G01N 33/53*    (2006.01)
*A61K 39/395*   (2006.01)

(52) U.S. Cl.
USPC ........................................ 435/7.1; 424/130.1

(58) Field of Classification Search
None
See application file for complete search history.

(56) References Cited

U.S. PATENT DOCUMENTS

2003/0219767 A1* 11/2003 Ayers et al. .................. 435/6

FOREIGN PATENT DOCUMENTS

WO    WO 2007/082352 A1    7/2007

OTHER PUBLICATIONS

Bengtsson et al (JBC, 2000, 275, 52: 40695-40702).*
Grover et al (Genomics, 1996, 38: 109-117).*
International Search Report for International Application No. PCT/SE2011/051289, mailed Feb. 16, 2012.
Grover et al. (2001); "Characterization and expression of murine PRELP," Matrix Biology 20: 555-564.
Grover et al. (1996); "The Gene Organization, Chromosome Location, and Expression of a 55-kDa Matrix Protein (PRELP) of Human Articular Cartilage," Genomics 38 (0605): 109-117.
Mikaelsson et al. (2005); "Fibromodulin, an extracellular matrix protein: characterization of its unique gene and protein expression in B-cell chronic lymphocytic leukemia and mantle cell lymphoma," Blood 105: 4828-4835.
Mikaelsson et al. (2010); "Small Leucine Rich Proteoglycans as Novel Tumor Markers in Chronic Lymphocytic Leukemia," Blood 116: Abstract 694.
Abba, M.C. et al. (2007) "Identification of Novel Amplification Gene Targets in Mouse and Human Breast Cancer at a Syntenic Cluster Mapping to Mouse ch8A1 and Human ch13q34," Cancer Research 67:4104-4112.
Bengtsson, E. et al. (1995) "The Primary Structure of a Basic Leucine-rich Repeat Protein, PRELP, Found in Connective Tissues," The Journal of Biological Chemistry 270(43):25639-25644.
Bengtsson, E. et al. (2000) "The Amino-terminal Part of PRELP Binds to Heparin and Heparan Sulfate," The Journal of Biological Chemistry 275(52):40695-40702.
Bengtsson, E. et al. (2002) "The Leucine-rich Repeat Protein PRELP Binds Perlecan and Collagens and May Function as a Basement Membrane Anchor," The Journal of Biological Chemistry 277(17):15061-15068.
Burger, J.A. et al. (2002) "Chemokine Receptors and Stromal Cells in the Homing and Homeostasis of Chronic Lymphocytic Leukemia B Cells," Leukemia & Lymphoma 43(3):461-466.
Caligaris-Cappio, F. (2000) "Biology of Chronic Lymphocytic Leukemia," Rev Clin Exp Hematol 4.1:5-21.
Daneshmanesh, A.H. (2008) "Ror1, a cell surface receptor tyrosine kinase is expressed in chronic lymphocytic leukemia and may serve as a putative target for therapy," Int. J. Cancer 123:1190-1195.
Edge, A.S.B. (2003) "Deglycosylation of glycoproteins with trifluoromethanesulphonic acid: elucidation of molecular structure and function," Biochem. J. 376:339-350.
Ferreira, A. et al. (1989) "Microtube formation and neurite growth in cerebellar macroneurons which develop in vitro: evidence for the involvement of the microtubule-associated proteins, MAP-1a, HMW-MAP2 and Tau," Developmental Brain Research 49:215-228.
Ghia, P. et al. (2005) "Differential Effects on CLL Cell Survival Exerted by Different Microenvironmental Elements," CTMI 294:135-145.
Grant, D.S. et al, (2002) "Decorin suppresses tumor cell-mediated angiogenesis," Oncogene 21:4765-4777.
Hallek, M. et al. (2008) "Guidelines for the diagnosis and treatment of chronic lymphocytic leukemia: a report from the International Workshop on Chronic Lymphocytic Leukemia updating the National Cancer Institute—Working Group 1996 guidelines," Blood 111(12):5446-5456.
Harris, N.L. et al. (2000) "The World Health Organization classification of neoplastic diseases of the haematopoietic and lymphoid tissues: report of the Clinical Advisory Committee Meeting, Airlie House, Virginia, Nov. 1997," Histopathology 36:69-86.

(Continued)

*Primary Examiner* — Sean Aeder
(74) *Attorney, Agent, or Firm* — Foley & Lardner LLP; Antoinette F. Konski

(57) ABSTRACT

The present invention relates to an in vitro method for assessing the risk that a subject suffers from a cancer, comprising measuring the expression level of Proline/arginine-rich end leucine repeat protein (PRELP) in cells from said subject, wherein an increased expression level of PRELP, as compared to healthy donors, indicates an increased probability of said subject suffering from cancer. It further relates to antibodies specific for PRELP and their use in diagnosis and therapy as well as a method for indicating a cell as a cancer cell.

15 Claims, 17 Drawing Sheets

(56) References Cited

OTHER PUBLICATIONS

Klein, U. et al. (2001) "Gene Expression Profiling of B Cell Chronic Lymphocytic Leukemia Reveals a Homogenous Phenotype Related to Memory B Cells," J. Exp. Med. 194(11):1625-1638.

Köhler, G. et al. (1975) "Continuous cultures of fused cells secreting antibody of predefined specificity," Nature 256:495-497.

Le Goff, M.M. et al. (2003) "Characterization of Opticin and Evidence of Stable Dimerization in Solution," The Journal of Biological Chemistry 278(46):45280-45287.

Månsson, B. et al. (2001) "Association of Chondroadherin with Collagen Type II," The Journal of Biological Chemistry 276(35):32883-32888.

Munk Pedersen, I. et al. (2004) "Microenvironmental Interactions and Survival of CLL B-cells," Leukemia & Lymphoma 45(12):2365-2372.

Rezvany, M.R. et al. (2000) "Autologous T lymphocytes may specificaly recognize leukaemic B cells in patients with chronic lymphocytic leukemia," British Journal of Haematology 111:608-617.

Rufo, A. et al. (2008) "The matrix PROLINE/Arginine-Rich End Leucin-Rich Repeat Protein (PRELP) impairs osteoclastogenesis by inhibiting NF-kappaB activity," Abstracts Bone 42: Abstract 52.

Scott, P.G. et al. (2004) "Crystal structure of the dimeric protein core of decorin, the archetypal small leucine-rich repeat proteoglycan," PNAS 101(44):15633-15638.

Scott, P.G. et al. (2006) "Crystal Structure of the Biglycan Dimer and Evidence That Dimerization is Essential for Folding and Stability of Class I Small Leucine-rich Repeat Proteoglycans," The Journal of Biological Chemistry 281(19):13324-13332.

Sztrolovics, R. et al. (1994) "Localization of the Human Fibromodulin Gene (FMOD) to Chromosome 1q32 and Completion of the cDNA Sequence," Genomics 23:715-717.

Vuillier, F. et al. (2005) "Lower levels of surface B-cell-receptor expression in chronic lymphocytic leukemia are associated with glycosylation and folding defects of the μ and CD79a chains," Blood 105(7):2933-2940.

Wendel-Hansen, V. et al. (1994) "Epstein-Barr Virus (EBV) Can Immortalize B-CLL Cells Activated by Cytokines," Leukemia 8(3):476-484.

Yamaguchi, Y. et al. (1988) "Expression of human proteoglycan in Chinese hamster ovary cells inhibits cell proliferation," Nature 336:244-246.

Yoshida, K. et al. (2002) "Leucine-rich repeat region of decorin binds to filamin-A," Biochimie 84:303-308.

International Preliminary Report on Patentability (IPRP) for International Application No. PCT/SE2011/051289, mailed Apr. 30, 2013, 11 pages.

\* cited by examiner

SEQUENCE LISTING

```
<160> NUMBER OF SEQ ID NOS: 18

<210> SEQ ID NO 1
<211> LENGTH: 135
<212> TYPE: PRT
<213> ORGANISM: Mus musculus
<220> FEATURE:
```

```
<221> NAME/KEY: DOMAIN
<222> LOCATION: (44)..(51)
<223> OTHER INFORMATION: CDRI
<220> FEATURE:
<221> NAME/KEY: DOMAIN
<222> LOCATION: (69)..(76)
<223> OTHER INFORMATION: CDRII
<220> FEATURE:
<221> NAME/KEY: DOMAIN
<222> LOCATION: (114)..(125)
<223> OTHER INFORMATION: CDRIII

<400> SEQUENCE: 1

Met Arg Met Leu Ser Val Leu Tyr Leu Leu Ser Ala Leu Pro Gly Ile
1               5                   10                  15

Leu Ser Glu Val Lys Leu Gln Gln Ser Gly Ala Glu Leu Val Lys Pro
            20                  25                  30

Gly Ala Ser Val Lys Leu Ser Cys Thr Ala Ser Gly Phe Asn Ile Lys
        35                  40                  45

Asp Thr Tyr Met His Trp Val Lys Gln Arg Pro Glu Gln Gly Leu Glu
    50                  55                  60

Trp Ile Gly Arg Ile Asp Pro Ala Asn Gly Asn Thr Lys Tyr Asp Pro
65                  70                  75                  80

Lys Phe Gln Gly Lys Ala Thr Ile Thr Ala Asp Thr Ser Ser Asn Thr
                85                  90                  95

Ala Tyr Leu Gln Leu Ser Ser Leu Thr Ser Glu Asp Thr Ala Val Tyr
            100                 105                 110

Tyr Cys Ala Arg Ser Thr Thr Val Val Val Asp Tyr Trp Gly Gln Gly
        115                 120                 125

Thr Thr Leu Thr Val Ser Ser
    130                 135

<210> SEQ ID NO 2
<211> LENGTH: 127
<212> TYPE: PRT
<213> ORGANISM: Mus musculus
<220> FEATURE:
<221> NAME/KEY: DOMAIN
<222> LOCATION: (48)..(53)
<223> OTHER INFORMATION: CDRI
<220> FEATURE:
<221> NAME/KEY: DOMAIN
<222> LOCATION: (71)..(73)
<223> OTHER INFORMATION: CDRII
<220> FEATURE:
<221> NAME/KEY: DOMAIN
<222> LOCATION: (109)..(118)
<223> OTHER INFORMATION: CDRIII

<400> SEQUENCE: 2

Met Asp Phe Gln Val Gln Ile Phe Ser Phe Leu Leu Ile Ser Ala Ser
1               5                   10                  15

Val Ile Leu Ser Arg Gly Asp Ile Leu Leu Thr Gln Thr Pro Ala Ile
            20                  25                  30

Lys Ser Ala Ser Pro Gly Glu Lys Val Thr Met Thr Cys Ser Ala Ser
        35                  40                  45

Ser Ser Ile Ser Tyr Met His Trp Tyr Gln Gln Lys Pro Gly Thr Ser
    50                  55                  60

Pro Lys Arg Trp Ile Tyr Asp Thr Ser Lys Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Ser Met Glu Ala Glu Asp Ala Ala Thr Tyr Tyr Cys His Gln Arg
```

```
            100                 105                 110
Ser Ser Tyr Pro Thr Phe Gly Ala Gly Thr Lys Leu Glu Leu Lys
        115                 120                 125

<210> SEQ ID NO 3
<211> LENGTH: 408
<212> TYPE: DNA
<213> ORGANISM: Mus musculus

<400> SEQUENCE: 3
atgagaatgt tgagtgttct gtacctgttg tcagcccttc ctggtatcct gtctgaggtg      60
aagctgcagc agtctggggc agagcttgtg aagccagggg cctcagtcaa gttgtcctgc     120
acagcttctg gcttcaacat taaagacacc tatatgcact gggtgaagca gaggcctgaa     180
cagggcctgg agtggattgg aaggattgat cctgcgaatg taatactaa  atatgacccg     240 aagttccagg gcaaggccac tataacagca gacacatcct ccaacacagc ctacctgcag     300
ctcagcagcc tgacatctga ggacactgcc gtctattact gtgctagatc tactacggta     360
gtagttgact actggggcca aggcaccact ctcacagtct cctcatag                 408

<210> SEQ ID NO 4
<211> LENGTH: 384
<212> TYPE: DNA
<213> ORGANISM: Mus musculus

<400> SEQUENCE: 4 atggatttc aggtgcagat tttcagcttc ctgctaatca gtgcctcagt catactgtcc       60
agaggagaca ttctgctgac ccagactcca gcaatcaagt ctgcatctcc aggggagaag     120
gtcaccatga cctgcagtgc cagctcaagt ataagttaca tgcactggta ccagcagaag     180
ccaggcacct cccccaaaag atggatttat gacacatcca aactggcttc tggagtccct     240
gctcgcttca gtggcagtgg gtctgggacc tcttattctc tcacaatcag cagcatggag     300
gctgaagatg ctgccactta ttactgccat cagcggagta gttaccccac gttcggtgct     360
gggaccaagc tggagctgaa atag                                            384

<210> SEQ ID NO 5
<211> LENGTH: 138
<212> TYPE: PRT
<213> ORGANISM: Mus musculus

<400> SEQUENCE: 5

Met Arg Met Leu Ser Val Leu Tyr Leu Leu Ser Ala Leu Pro Gly Ile
1               5                   10                  15

Leu Ser Glu Val Gln Leu Gln Glu Ser Gly Ala Glu Leu Ala Arg Pro
            20                  25                  30

Gly Ala Ser Val Lys Met Ser Cys Lys Ala Ser Gly Tyr Thr Phe Thr
        35                  40                  45

Ser Tyr Thr Met His Trp Val Lys Gln Arg Pro Gly Gln Gly Leu Glu
    50                  55                  60

Trp Ile Gly Tyr Ile Asn Pro Ser Ser Gly Tyr Thr Asn Tyr Asn Gln
65                  70                  75                  80

Lys Phe Lys Asp Lys Ala Thr Leu Thr Ala Asp Lys Ser Ser Ser Thr
                85                  90                  95

Ala Tyr Met Gln Leu Ser Ser Leu Thr Ser Glu Asp Ser Ala Val Tyr
            100                 105                 110

Tyr Cys Ala Ser Pro Tyr Tyr Gly Tyr Gly Tyr Ala Met Asp Tyr Trp
        115                 120                 125
```

Gly Gln Gly Thr Ser Val Thr Val Ser Ser
    130                 135

<210> SEQ ID NO 6
<211> LENGTH: 414
<212> TYPE: DNA
<213> ORGANISM: Mus musculus

<400> SEQUENCE: 6
atgagaatgt tgagtgttct gtacctgttg tcagcccttc ctggtatcct gtctgaggtg    60
cagctgcagg agtctggggc tgaactggca agacctgggg cctcagtgaa gatgtcctgc   120
aaggcttctg gctacacctt tactagctac acgatgcact gggtaaaaca gaggcctgga   180
cagggtctgg aatggattgg atacattaat cctagcagtg gttatactaa ttacaatcag   240
aagttcaagg acaaggccac attgactgca gacaaatcct ccagcacagc ctacatgcaa   300
ctgagcagcc tgacatctga ggactctgca gtctattact gtgcaagtcc ttactacggc   360
tacggctatg ctatggacta ctggggtcaa ggaacctcag tcaccgtctc ctca         414

<210> SEQ ID NO 7
<211> LENGTH: 20
<212> TYPE: PRT
<213> ORGANISM: Homo sapiens

<400> SEQUENCE: 7

Met Arg Ser Pro Leu Cys Trp Leu Leu Pro Leu Leu Ile Leu Ala Ser
1               5                   10                  15

Val Ala Gln Gly
            20

<210> SEQ ID NO 8
<211> LENGTH: 10
<212> TYPE: PRT
<213> ORGANISM: Homo sapiens

<400> SEQUENCE: 8

Cys Phe Arg Leu Leu Gln Ser Val Val Ile
1               5                   10

<210> SEQ ID NO 9
<211> LENGTH: 22
<212> TYPE: DNA
<213> ORGANISM: Artificial Sequence
<220> FEATURE:
<223> OTHER INFORMATION: PRELP RT-PCR primer, sense

<400> SEQUENCE: 9
tcaagaacct catgcagctc aa                                              22

<210> SEQ ID NO 10
<211> LENGTH: 23
<212> TYPE: DNA
<213> ORGANISM: Artificial Sequence
<220> FEATURE:
<223> OTHER INFORMATION: PRELP RT-PCR primer, antisense

<400> SEQUENCE: 10
atctgggttc cgttgatttt ctc                                             23

<210> SEQ ID NO 11
<211> LENGTH: 24
<212> TYPE: DNA
<213> ORGANISM: Artificial Sequence

```
<220> FEATURE:
<223> OTHER INFORMATION: beta-actin RT-PCR primer, sense

<400> SEQUENCE: 11
attaaggaga agctgtgcta cgtc                                           24

<210> SEQ ID NO 12
<211> LENGTH: 24
<212> TYPE: DNA
<213> ORGANISM: Artificial Sequence
<220> FEATURE:
<223> OTHER INFORMATION: Beta-actin RT-PCR primer, antisense

<400> SEQUENCE: 12
atgatggagt tgaaggtagt ttcg                                           24

<210> SEQ ID NO 13
<211> LENGTH: 20
<212> TYPE: DNA
<213> ORGANISM: Artificial Sequence
<220> FEATURE:
<223> OTHER INFORMATION: PRELP RT-QPCR primer, sense

<400> SEQUENCE: 13
tgccttcatt cggcttaact                                                20

<210> SEQ ID NO 14
<211> LENGTH: 23
<212> TYPE: DNA
<213> ORGANISM: Artificial Sequence
<220> FEATURE:
<223> OTHER INFORMATION: PRELP RT-QPCR primer, antisense

<400> SEQUENCE: 14
atctgggttc cgttgatttt ctc                                            23

<210> SEQ ID NO 15
<211> LENGTH: 24
<212> TYPE: DNA
<213> ORGANISM: Artificial Sequence
<220> FEATURE:
<223> OTHER INFORMATION: PRELP RT-QPCR probe
<220> FEATURE:
<221> NAME/KEY: misc_feature
<222> LOCATION: (1)..(1)
<223> OTHER INFORMATION: Blue-6-FAM
<220> FEATURE:
<221> NAME/KEY: misc_feature
<222> LOCATION: (24)..(24)
<223> OTHER INFORMATION: TAMRA

<400> SEQUENCE: 15
tccacctgtc ccacaacagg atca                                           24

<210> SEQ ID NO 16
<211> LENGTH: 20
<212> TYPE: DNA
<213> ORGANISM: Artificial Sequence
<220> FEATURE:
<223> OTHER INFORMATION: Beta-actin RT-QPCR primer, sense

<400> SEQUENCE: 16
cgacaggatg cagaaggaga                                                20

<210> SEQ ID NO 17
<211> LENGTH: 20
<212> TYPE: DNA
<213> ORGANISM: Artificial Sequence
```

```
-continued

<220> FEATURE:
<223> OTHER INFORMATION: Beta-actin RT-QPCR primer, antisense

<400> SEQUENCE: 17
cgtcatactc ctgcttgctg                                                    20

<210> SEQ ID NO 18
<211> LENGTH: 27
<212> TYPE: DNA
<213> ORGANISM: Artificial Sequence
<220> FEATURE:
<223> OTHER INFORMATION: Beta-actin RT-QPCR probe
<220> FEATURE:
<221> NAME/KEY: misc_feature
<222> LOCATION: (1)..(1)
<223> OTHER INFORMATION: Blue-6-FAM
<220> FEATURE:
<221> NAME/KEY: misc_feature
<222> LOCATION: (27)..(27)
<223> OTHER INFORMATION: TAMRA

<400> SEQUENCE: 18
aagatcaaga tcattgctcc tcctgag                                            27
```

DIAGNOSTIC AND THERAPEUTIC TARGET

CROSS-REFERENCE TO RELATED APPLICATIONS

This application is a national stage application under 35 U.S.C. §371 of International Application No. PCT/SE2011/051289, filed Oct. 28, 2011, which in turn claims priority to Swedish Patent Application No. 1051158-2, filed Nov. 5, 2010, and claims priority under 35 U.S.C. §119(e) to U.S. Provisional Patent Application No. 61/407,556, filed Oct. 28, 2010, the contents of which are hereby incorporated by reference in their entireties into the present disclosure.

SEQUENCE LISTING

The instant application contains a Sequence Listing which has been submitted in ASCII format via EFS-Web and is hereby incorporated by reference in its entirety. Said ASCII copy, created on May 17, 2013, is named 102796-0160_SL.txt and is 8,890 bytes in size.

FIELD OF THE INVENTION

The present invention relates to the field of therapy and diagnosis of cancer. More specifically, it relates to therapy and diagnosis of cancers of tissues and organs originating from ectoderm, mesoderm and endoderm, and to products useful in such therapies and diagnosis.

BACKGROUND OF THE INVENTION

The microenvironment is important for the proliferation and survival of chronic lymphocytic leukemia (CLL) cells.[1,2] Various cell types may contribute to provide signals and release factors that prevent apoptosis of CLL cells.[3,4] Molecules that facilitate the interaction between the leukemic cells and the microenvironment may be critical in the pathophysiology of CLL and potentially serve as structures for targeted therapies.

In 2001, gene expression profiling in CLL showed an increased expression of the extracellular matrix (ECM) protein fibromodulin (FMOD).[5] FMOD is a member of the small leucine-rich proteoglycan family (SLRP) and is normally expressed in collagen-rich tissues. We demonstrated that FMOD was expressed at the gene and protein level in CLL and mantle cell lymphoma (MCL).[6] Cluster regulation of genes has been reported in malignant diseases.[7] The proline/arginine-rich end leucine-rich repeat protein (PRELP) has a structure closely related to FMOD and is located about 80 kb 3'-proximal to FMOD on chromosome 1q32.1.[8] PRELP has a molecular weight (MW) of 55 kDa and is normally expressed in the extracellular matrix of connective tissues, mainly in cartilage, lung, kidney, skin, and tendon.[9,10] The function of PRELP is unclear, but the interactions between PRELP and collagen type I and II as well as heparin and heparan sulphates[11,12] suggest that PRELP may be a molecule anchoring basement membranes to connective tissue.[12]

SUMMARY OF THE INVENTION

Overexpression of genes in tumor cells might be due to epigenetic regulations which may span a cluster of closely located genes. Following our previous studies on FMOD[6] and ROR-1[13] in CLL, both located on chromosome 1, the present study was initially undertaken to explore the gene and protein expression of PRELP in CLL and other hematological malignancies, in our endeavour to explore uniquely expressed molecules in CLL which might play a role in the pathobiology of the disease.

PRELP naturally is a secreted protein. The present inventor has shown that in cancer cells not only is it not secreted but sequestered inside the cancer cells. Also a fraction of this unprocessed protein is expressed on cell surface, cf. FIG. 14. This has been found for leukemic cells and also for cancer cells originating from the embryonic germ layers of ectoderm, mesoderm and endoderm. It has also been found that antibodies raised against PRELP induce apoptosis in cancer cells expressing PRELP on the cell surface.

The present inventor has found that PRELP is expressed in CLL and a human Burkitt's lymphoma cell line (Raji). Burkitt's lymphoma is a cancer of lymphatic system in particular B lymphocyte. Chronic lymphocytic leukemia is also a cancer of B lymphocyte. Expression of PRELP in both lymphoma and leukemia with B lymphocyte origin formulates the PRELP as a therapeutic target in B cell malignancies with no expression of PRELP in normal B cells. Apart from B cell malignancies, PRELP is also expressed in solid tumors listed in Table 1. According to these data PRELP is expressed in Breast cancer, Ovarian cancer, and prostate cancer as well as in tumors of neuroblatoma, glioblastoma, and medulablastoma.

The following tissues and organs derive from three embryonic germ layers of Ectoderm, Mesoderm, and Endoderm: Breast tissue derives from ectoderm and mesoderm. Central nervous system derives from ectoderm. Ovary, lymphatic systems, and bone tissues including blood cells derive from mesoderm, and finally prostate derives from endoderm.

Although expression of PRELP has not been shown in all cancers, the origin of tissues and organs plus expression of PRELP in the above mentioned cancers (as representative for each embryonic layer) would ratify PRELP as a universal tumor marker, especially in the immature preproprotein (precursor) format. Even if the PRELP is expressed in corresponding normal tissues, the cell surface expression of PRELP in precursor format would be an advantage for targeting cancer cells without harming the normal cells. In conclusion, two distinct properties of precursor and cell surface expression of PRELP in cancer cells makes it an ideal target (FIG. 14) for detection of such cancer cells as well as for therapy and diagnosis of such cancers as discussed herein In a first aspect, the invention relates to an in vitro method for assessing the risk that a subject suffers from cancers of tissues or organs derived from the three embryonic layers of ectoderm, mesoderm and endoderm, comprising measuring the expression level of Proline/arginine-rich end leucine repeat protein (PRELP) in cells from said subject, wherein an increased expression level of PRELP, as compared to healthy donors, indicates an increased probability of said subject suffering from said cancer.

In a further aspect, the invention relates to an affinity binder, or antigen binding fragment thereof, specific for the 38 kDa form of PRELP.

In a further aspect, the invention relates to an affinity binder, antibody or antigen binding fragment thereof, according to the above aspect, for use in therapy, particularly in cancer therapy and especially in therapy of breast cancer, ovarian cancer, prostate cancer, glioblastoma, Burkitt's lymphoma, neuroblastoma, medullablastoma, chronic lymphocytic leukemia (CLL) or mantle cell lymphoma (MCL). Such affinity binders may be "armed", i.e. bound to a moiety that has a toxic effect on cells, particularly cancer cells. Such moieties are known to the skilled person, cf Polakis P. Arming antibodies for cancer therapy. Curr Opin Pharmacol 2005; 5: 382-7.

In a further aspect, the invention relates to a method for treatment of a cancer, comprising administering an affinity binder, or antigen binding fragment thereof, specific for PRELP to a subject suffering from a cancer.

In a further aspect, the invention relates to a method of indicating a cell as a cancer cell, comprising detecting a presence or non-presence of PRELP on the surface of said cell, wherein the presence of PRELP on said surface of said cell indicates that said cell is a cancer cell. Such detection may be done using an affinity binder specific for PRELP, optionally conjugated to a detectable moiety such as a fluorescent moiety, in routine detection methods known to the skilled person.

Preferred embodiments are set out in the dependent claims.

B) Western blot at non-reducing and reducing conditions using anti-PRELP monoclonal antibody clone 1C10-C3. Lane 1. Cell line MDA lysate (human breast cancer), Lane 2. Cell line U373 lysate (Human glioblastoma), Lane 3. Cell line PC3 lysate (Human prostate cancer), Lane 4. Cell lysate of a human healthy PBMC. The Ig respective bands reveals after reducing. The 34 kDa band corresponds to PRELP. Appearance of Ig heavy and light chains in Western blots are due to cross-reactivity of seconday antibody with human immunoglobulins. Anti-PRELP clone 1C10-C3 used as primary antibody. HRP-conjugated sheep anti-mouse was used as secondary antibody in this experiment.

Figure 10:
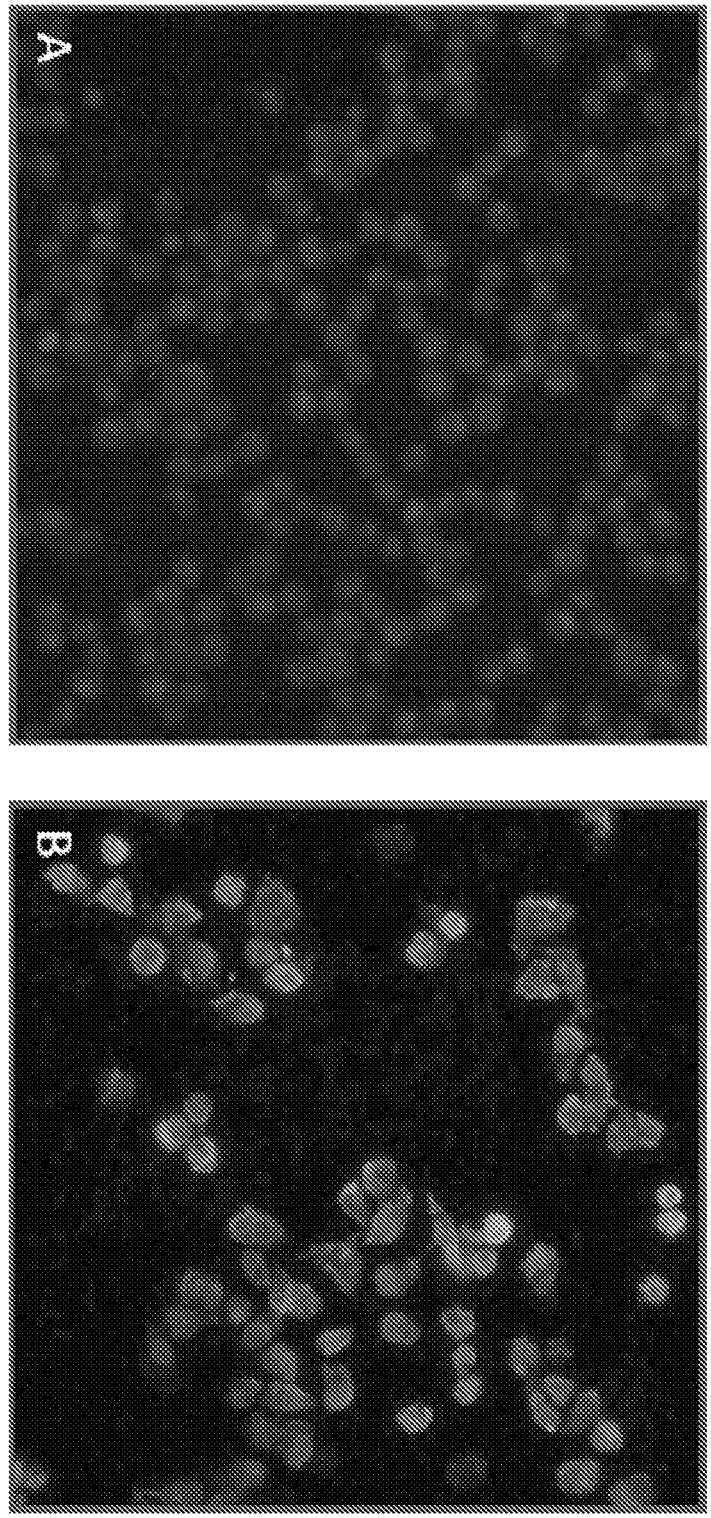

FIG. 10. Immunocytochemistry (ICC) on human breast cancer cell line SKBR3. A) SKBR3 cells stained with irrelevant mouse IgM as isotype control. B) SKBR3 cells stained with anti-PRELP monoclonal antibody clone 1C10-C3. FITC-conjugated sheep anti-mouse was used as secondary antibody.

Figure 11:
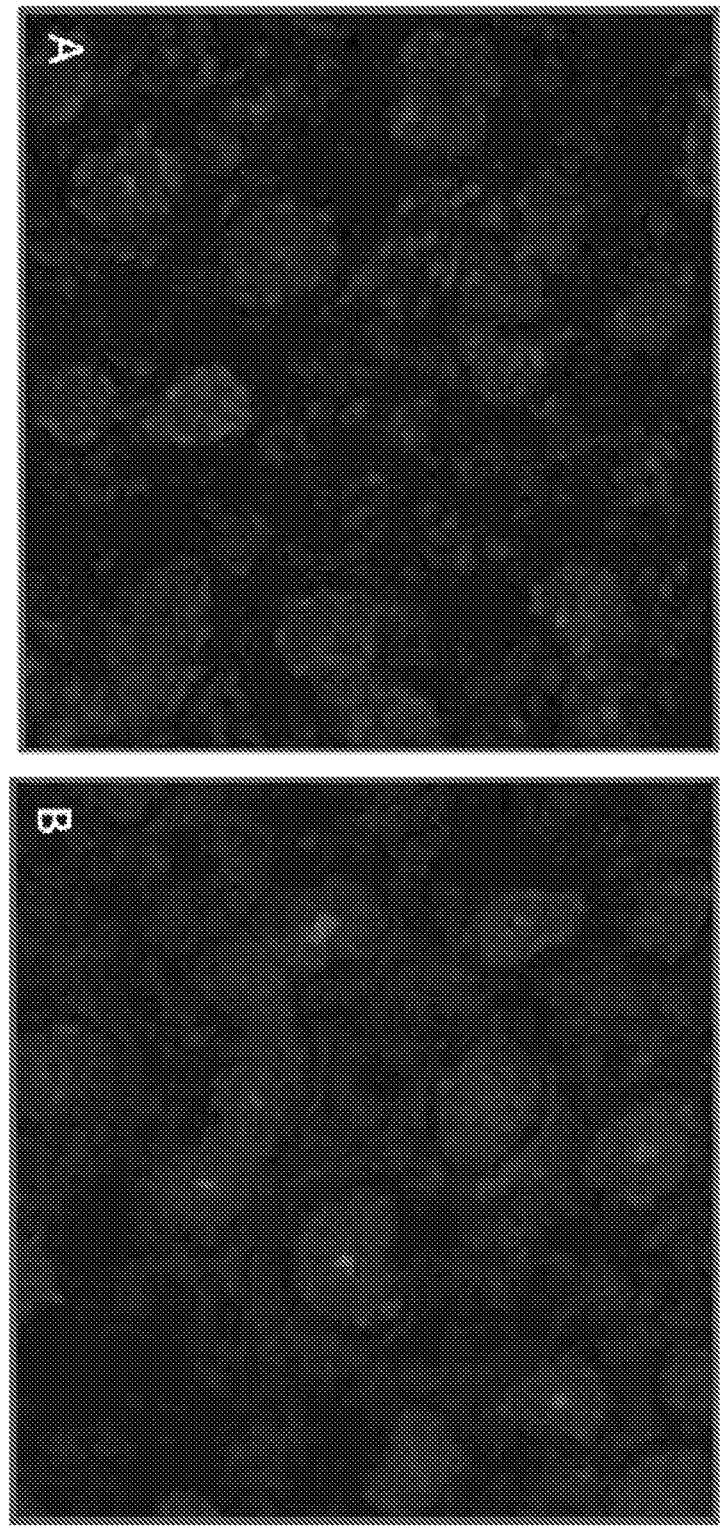

FIG. 11. Immunohistochemistry (IHC) on human normal breast tissues. A) irrelevant mouse IgM as isotype control. B) anti-PRELP monoclonal antibody clone 1C10-C3. FITC-conjugated sheep anti-mouse was used as secondary antibody.

Figure 12:
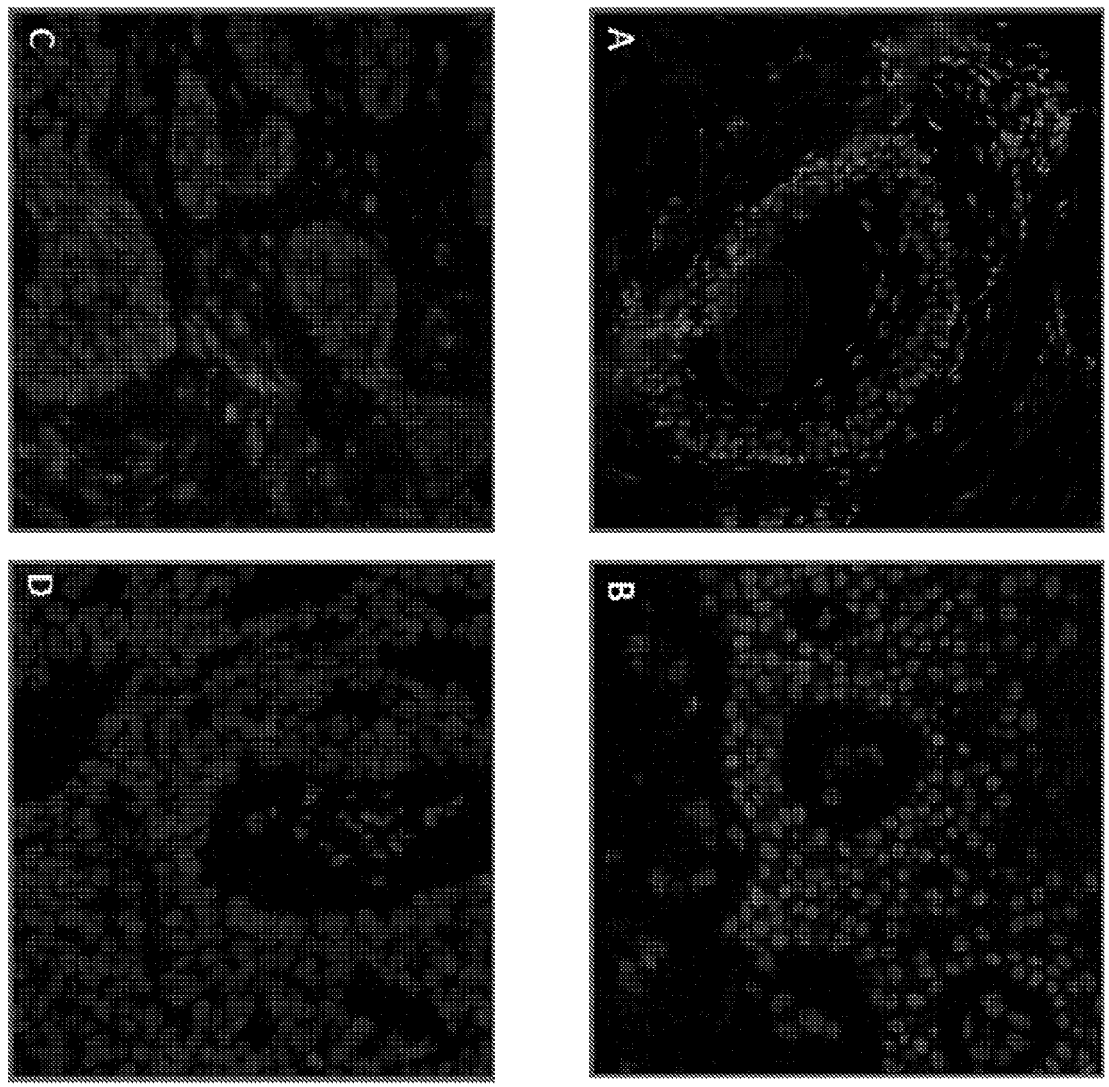

FIG. 12. Immunohistochemistry (IHC) on human normal tissues. A and B) human skin tissue from a 26-year old male stained with irrelevant mouse IgM as isotype control and anti-PRELP monoclonal antibody clone 1C10-C3, respectively.

B and C) human skin tissue from a 67-year old female stained with irrelevant mouse IgM as isotype control and anti-PRELP monoclonal antibody clone 1C10-C3, respectively. No expression of PRELP was observed in skin tissues of these two normal individuals. FITC-conjugated sheep anti-mouse was used as secondary antibody.

Figure 13:
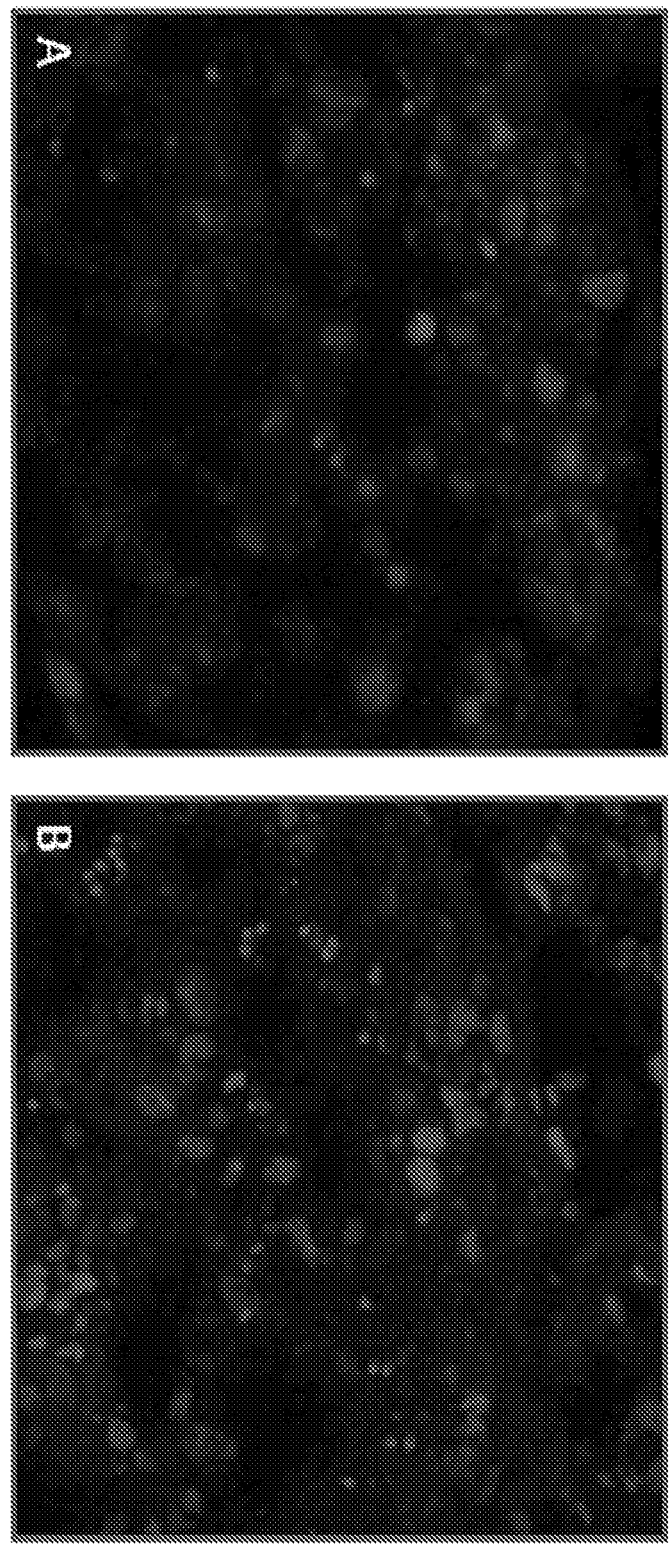

FIG. 13. Immunohistochemistry (IHC) on human normal testis tissues. Testis tissue was obtained from a 49 year-old male 24 hrs after death. A) irrelevant mouse IgM as isotype control. B) anti-PRELP monoclonal antibody clone 1C10-C3. FITC-conjugated sheep anti-mouse was used as secondary antibody. No expression of PRELP was observed in testis tissue.

Figure 14:
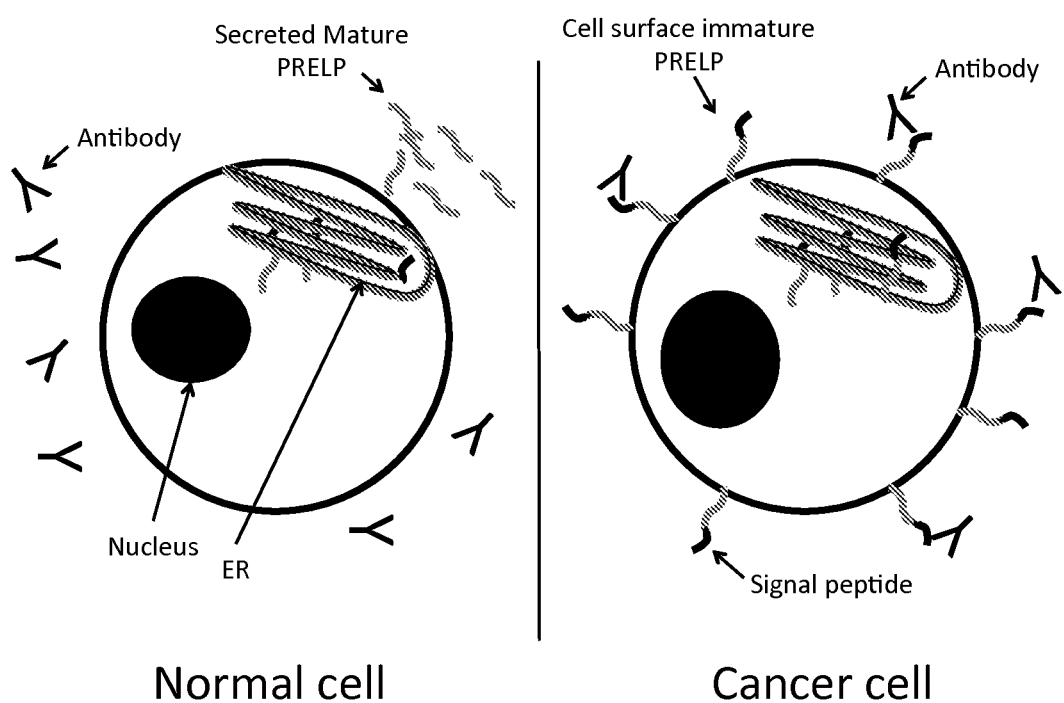

FIG. 14. Schematic representation of interaction of anti-PRELP antibody with cancer cells for both diagnosis and therapy. The diagram shows expression of PRELP in a normal cell as a secreted mature protein. In a normal cell the precursor protein synthesized in endoplasmic reticulum (ER). Upon cleavage of signal peptide by signal peptidases the mature protein will be secreted to the extracellular matrix. As the anti-signal antibody is against signal peptide, it cannot interact with mature PRELP protein lacking the signal peptide, remaining harmless (left panel). In a cancer cell to as yet unknown reason the expressed PRELP will be in a precursor format unable to secret but expressed on the cell surface either intact or anchored to an unknown protein. This cell surface-precursor PRELP can be recognized by and interact with anti-signal antibody leading to induction of apoptosis. Generating antibody against any other part of PRELP apart from signal peptide for in vivo treatment would cause interaction with secreted PRELP (in extracellular matrix) leading to generation of antibody-antigen complex with subsequent mediating immune response triggering tissue damage. But antibodies against whole part of PRELP may be used as a tool for detecting PRELP and diagnosis of cancer according to the invention.

SEQUENCES

SEQ ID NO: 1: VH (anti-PRELP-SS clone 6G1-G11), Mouse IgM isotype.
SEQ ID NO: 2: VL (anti-PRELP-SS clone 6G1-G11), Mouse kappa chain
SEQ ID NO: 3: DNA sequence encoding VH (anti-PRELP-SS clone 6G1-G11), Mouse IgM isotype
SEQ ID NO: 4: DNA sequence encoding VL (anti-PRELP-SS clone 6G1-G11), Mouse kappa chain
SEQ ID NO: 5: Anti-PRELP-SS VH clone HB35-G11
SEQ ID NO: 6: DNA sequence encoding Anti-PRELP-SS VH clone HB35-G11
SEQ ID NO: 7: N-terminal part of PRELP (signal peptide)
SEQ ID NO: 8: C-terminal part of PRELP

DETAILED DESCRIPTION OF THE INVENTION

The present study demonstrates that an unglycosylated 38 kDa PRELP protein seems to be exclusively expressed in CLL leukemic cells, CLL cell lines, MCL cells, Burkitt's lymphoma cells, breast cancer cells, ovarian cancer cells, prostate cancer cells, and glioblastoma cells. Other hematological malignancies as well as PBMC of normal donors did not express PRELP. Strong polyclonal activation (PMA/ionomycin) of normal B and T lymphocytes did not induce expression of PRELP (data not shown), suggesting that the expression of the 38 kDa PRELP in CLL might reflect a constitutive aberration in vivo.

Figure 1:
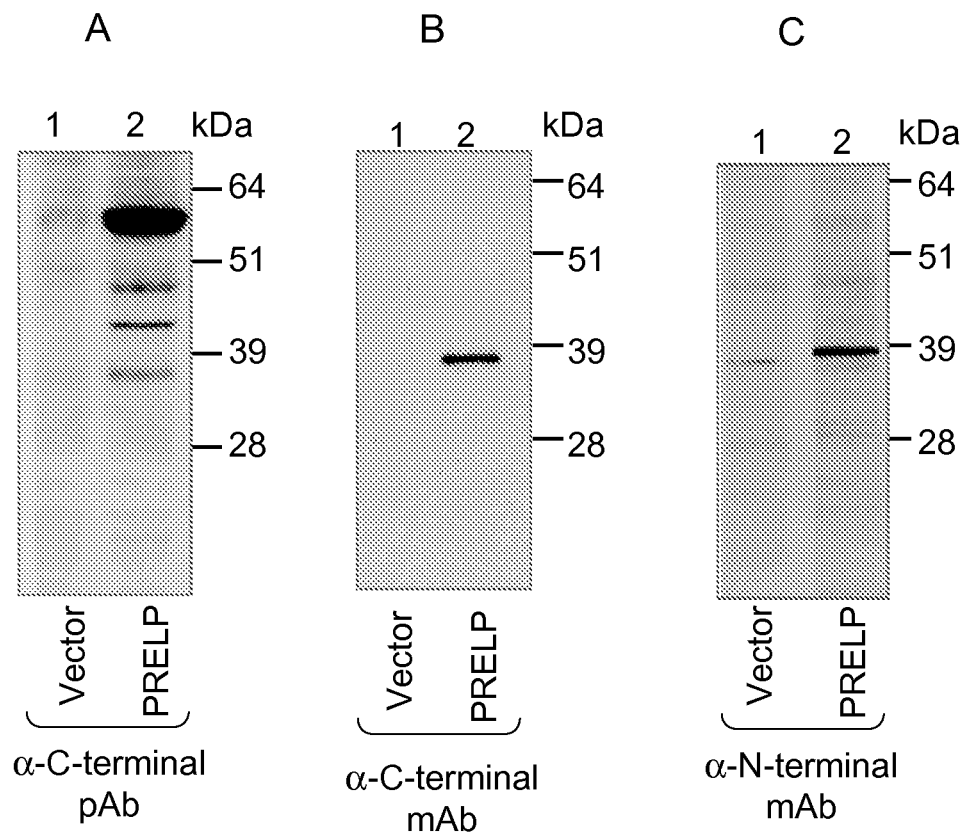
FIG. 1. Western blot analyses to validate the specificity of the anti-PRELP antibodies. The precursor PRELP gene was cloned into pCMV6-Neo vector and transfected into mouse SP2/0 cell line. Lane 1: Cell lysate of SP2/0 cells transfected with the vector alone (negative control). Lane 2: Cell lysate of SP2/0 cells transfected with the PRELP construct. Recombinant PRELP was detected using A) rabbit anti-C-terminal PRELP polyclonal antibody recognizing unglycosylated and glycosylated forms of recombinant PRELP (38 kDa, 44 kDa, 48 kDa and 55-58 kDa); B) mouse monoclonal antibody anti-C-terminal PRELP and C) mouse monoclonal antibody anti-N-terminal PRELP recognizing non-glycosylated PRELP (38 kDa).

PRELP is normally secreted into the extracellular matrix compartment but its function is not clearly known. The mature PRELP proteins (50 and 58 kDa), which were detected in serum of both CLL patients and healthy donors are probably produced by fibroblasts. However, in CLL cells, a unique 38 kDa PRELP protein was identified. Mutation analysis of the PRELP gene in CLL did not reveal any substantial nucleotide aberrations which could explain the difference at the protein level. No nucleotide mutations in the C-terminal region (against which our C-terminal antibody was raised) were found. These findings, in combination with the small number of coding exons (only 2 exons) make splice variants or truncation unlikely. The CLL specific 38 kDa PRELP was detected by a monoclonal antibody against the PRELP signal peptide indicating that the signal peptide was not cleaved off. Furthermore, the CLL specific 38 kDa PRELP was not detected in serum. This could be due to impaired secretion from leukemic cells and retention in subcellular organelles or, alternatively, rapid degradation in the serum by proteases. The presence of an intact signal peptide may suggest retention in the cytosol. Impaired glycosylation and retained signal peptide may be specific for CLL, as PRELP expressed in SP2/0 cells seems to be fully matured and processed, i.e translocated, glycosylated and with the signal peptide cleaved off (FIG. 1). Similar observations have been reported for the mu- and CD79a chains on the surface of CLL cells.[21]

The difference between normal PRELP (50-58 kDa) and CLL-derived PRELP (38 kDa) may be due to post-translational modifications. Complete deglycosylation of yeast-derived PRELP resulted in a 38 kDa PRELP, corresponding in size to PRELP detected in CLL, possibly the PRELP core protein with no side-chain glycan modifications.

Stable dimerization of several SLRPs including opticin, decorin, biglycan, and chondroadherin[22-25] support the suggestion of a dimerized PRELP in CLL. Formation of PRELP dimers may be analogous to the proposed model of opticin dimerization.[22] In this model the amino terminal of the dimer was accessible to antibodies which could explain the reactivity of our N-terminal antibody with the dimerized PRELP. Fractionation analyses of CLL cells indicated that the dimerized PRELP is located in the cytoskeletal and membrane fractions.

This is the first study associating PRELP with CLL. There are reports linking other SLRPs to cancer. Decorin suppresses cell growth and tumor cell mediated angiogenesis.[26,27] Decorin and the other SLRPs are secreted proteins that normally mediate their functions by binding to membrane receptors or extracellular matrix proteins. However, other locations and functions have been reported. An intracellular role has been proposed for decorin in binding the cytoskeletal protein, filamin.[28] PRELP has been shown to bind and inhibit NF-kappa B activity in the nucleus of osteoclasts.[29]

Our findings suggest a non-secreted 38 kDa PRELP in CLL but the role is not clear. However, the specific and unique expression of a 38 kDa PRELP protein strongly indicates a functional role in CLL. The specific expression of another proteoglycan, FMOD[6] in CLL may suggest a role of proteoglycans in CLL. Furthermore, preliminary data indicate that another SLRP, opticin, located in close proximity to FMOD and PRELP on chromosome 1 (1q32) is also upregulated in CLL. The functional characterization of these proteoglycans in CLL is urgently warranted to understand their biological importance.

Further experiments showing the expression of PRELP in Raji, a human Burkitt's lymphoma cell line added clues to the possibility of expression of PRELP in other hematological malignancies or even solid tumors. To investigate the expression of PRELP in solid tumors a panel of cell lines was selected. The reason for selecting the cell line is the ease of separating the cells to detect the surface expression by flow cytometry technique. The adherent cells were retrieved without trypsinization, as this may alter the structure of surface antigens leading to false results. It is of note that surface expression of PRELP in tumor cells is crucial in targeting the cancer cells. PRELP is not expressed on the surface of normal cells.

Expression of PRELP in breast, ovary, prostate cancer cell lines as well as in glioblastoma cells and also lack of surface expression in normal cells further verifies the use of this unique structure in targeting the cancer cells by means of monoclonal antibody. Our antibodies are raised against the signal peptide of PRELP, where it is cleaved off in normal conditions in endoplasmic reticulum before secretion to the extracellular matrices. This is the most important issue, which makes the cell surface-expressed PRELP in tumor cells as a very unique and also safe target with no interaction with any other PRELP molecules expressed by other normal tissues.

To investigate this subject, normal tissues especially PBMC, breast, testis, and skin were obtained and PRELP expression was studied. No expression of PRELP was found in these normal tissues using three different clones of anti-PRELP antibodies. High level of PRELP expression in three different breast cancer cell lines, SKBR3, MDA, and BT474 as well as three ovarian carcinoma cell lines A2780S, 2008C13R, and CaOv4 with no expression in a healthy breast strongly suggest the ectopic expression of PRELP in such tumors making this molecule a good candidate for targeting. We have also shown that anti-PRELP antibody can induce apoptosis in CLL cells. This function may confer to any other cells expressing PRELP. In general we suggest that anti-PRELP antibodies generated specifically against signal peptide might be used for targeting breast cancer, ovarian caner, prostate cancer, chronic lymphocytic leukemia, Burkitt's lymphoma, glioblastoma, neuroblastoma, and medullablastoma without harming at least tissues of skin, breast, testis, and most importantly peripheral blood mononuclear cells.

DEFINITIONS

The term "Affinity binder" shall be construed as any molecular entity capable of selectively binding to an analyte of interest. Affinity binders may be polyclonal or monoclonal antibodies, fragments thereof such as F(ab')$_2$, Fab, Fab', Fv, Fc, and Fd fragments, which may be incorporated into single domain antibodies, single-chain antibodies, maxibodies, minibodies, intrabodies, diabodies, triabodies, tetrabodies, v-NAR and bis-scFv. Affinity binders also include synthetic binding molecules such as molecularly imprinted polymers, affibodies or any other affinity binder. In the aspects of the invention using antibodies, the antibodies may be substituted for other types of affinity binders as applicable.

Affinity between two entities means an affinity of at least $10^6$, $10^7$, $10^8$ $10^9$ M$^{-1}$, or $10^{10}$ M$^{-1}$. Affinities greater than $10^8$ M$^{-1}$ are preferred.

The term "specific for" indicates that the variable regions of the antibodies, or binding molecules, recognize and bind PRELP according to the invention exclusively (i.e., able to distinguish PRELP from other similar polypeptides despite sequence identity, homology, or similarity found in the family of polypeptides), but may also interact with other proteins (for example, S. aureus protein A or other antibodies in ELISA techniques) through interactions with sequences outside the variable region of the antibodies, and in particular, in the constant region of the molecule. Screening assays in which one can determine binding specificity of an anti-PRELP antibody are well known and routinely practiced in the art. (Chapter 6, Antibodies A Laboratory Manual, Eds. Harlow, et I al., Cold Spring Harbor Laboratory; Cold Spring Harbor, N.Y. (1988), herein incorporated by i reference in its entirety).

An "immunogenic agent" or "immunogen" is capable of inducing an immunological response against itself on administration to a patient, optionally in conjunction with an adjuvant.

Antibodies that recognize the same epitope can be identified in a simple immunoassay showing the ability of one antibody to block the binding of another antibody to a target antigen. T-cells recognize continuous epitopes of about nine amino acids for CD8 cells or about 13-15 amino acids for CD4 cells. T cells that recognize the epitope can be identified by in vitro assays that measure antigen-dependent proliferation, as determined by 3H-thymidine incorporation by primed T cells in response to an epitope (Burke et al., J. Inf. Dis. 170, 1110-19 (1994)), by antigen-dependent killing (cytotoxic T lymphocyte assay, Tigges et al., J. Immunol. 156, 3901-3910) or by cytokine secretion.

When practicing the present invention the person skilled in the art may further make of use conventional techniques in the field of pharmaceutical chemistry, immunology, molecular biology, microbiology, cell biology, transgenic animals and recombinant DNA technology, as i.a. disclosed in Sambrook et al. "Molecular cloning: A laboratory manual", $3^{rd}$ ed. 2001; Ausubel et al. "Short protocols in molecular biology", $5^{th}$ ed. 1995; "Methods in enzymology", Academic Press, Inc.; MacPherson, Hames and Taylor (eds.). "PCR 2: A practical approach", 1995; "Harlow and Lane (eds.) "Antibodies, a laboratory manual" 1988; Freshney (ed.) "Culture of animal cells", $4^{th}$ ed. 2000; Hogan et al. "Manipulating the Mouse Embryo: A Laboratory Manual", Cold Spring Harbor Laboratory, 1994; or later editions of these books.

EXAMPLES

The following examples serve to illustrate the invention and shall not be considered as limiting the scope of the invention, which is that of the claims.

Materials and Methods

Patients and Controls

The diagnosis of CLL and disease status (progressive/non-progressive) were established as described[13] using the WHO classification of hematopoetic and lymphoid malignancies and the modified NCI criteria.[14,15] Clinical characteristics of the patients are shown in Table 1. Heparinized blood was collected as the source of leukemic cells from patients with CLL (n=30), MCL (n=5), hairy cell leukemia (HCL) (n=2), B-cell prolymphocytic leukemia (B-PLL) (n=1), T-cell prolymphocytic leukemia (T-PLL) (n=4), chronic myelogenous leukemia (CML) (n=5), acute myelogenous leukemia (AML) (n=5) and acute lymphoblastic leukemia (ALL) (n=10). Bone marrow tumor cells were obtained from patients with multiple myeloma (MM) (n=6), and follicular lymphoma (FL) (n=2). Blood was also drawn from healthy control donors (n=10). Serum was collected from CLL patients (n=8) and healthy controls (n=8). All samples were collected with informed consent of the patients and approval from the local ethical committee.

Hematological and Fibroblast Cell Lines

Four CLL cell lines and nine cell lines derived from a variety of other hematological malignancies were included; CLL (EHEB, 183-E95, 232-B4, WAC3-CD5), MM (LP-1), T-cell leukemia (SKW3), ALL (HUT-78, HPB-ALL, MOLT-4, JURKAT), AML (HL60), CML (K562), and NK cell lymphoma (YT). EHEB and YT were obtained from DSMZ (Braunschweig, Germany). The other CLL cell lines (183-E95, 232-B4, WAC3-CD5)[16] were a kind gift from Prof. Anders Rosén (Linkoping University, Sweden) and Prof Kenneth Nilsson (Uppsala University, Sweden). The remaining cell lines were provided by the National Cell Bank of Iran (NCBI, Pasteur Institute of Iran, Tehran, Iran). All cell lines were adapted to grow in RPMI-1640 medium (Gibco, Paisley, Scotland) supplemented with 10% fetal bovine serum (FBS) (Gibco), L-glutamine (2 mM), penicillin (100 U/ml) and streptomycin (100 µg/ml) (Gibco).

Isolation of Cells

Peripheral blood mononuclear cells (PBMC) (lymphocytes and monocytes) from normal donors and leukemic cells from blood and bone marrow were isolated using Ficoll-Paque Plus (GE Healthcare, Bio-sciences AB, Buckinghamshire, UK) density-gradient centrifugation, as described.[17] Granulocytes, leukemic B-cells, normal T and B lymphocytes were isolated as described.[6] The purity of the isolated populations was tested by direct immunofluorescence using monoclonal antibodies against CD3, CD19, and CD14 (BD Biosciences, San Jose, Calif., USA).

RT-PCR and RT-QPCR Amplification of PRELP mRNA

Total RNA was extracted from leukemic cells and normal PBMC using RNAzol B reagent (BioSite, Täby, Sweden) according to manufacturer's instruction. First strand cDNA was synthesized as described.[6] PCR amplification was performed using PRELP specific primers (Table 2). Briefly, 25 µµl of PCR reaction mixture was prepared using 2.5 µl of 10× buffer, 2 µl of 25 mM $MgCl_2$, 1.5 µl dNTPs (10 mM), 5 µmol of each primer and 1 unit of Ampli-Taq Gold DNA polymerase (Perkin-Elmer/Applied Biosystems, Boston, Mass., USA). PCR was performed in 35 cycles, initiated by 1 cycle at 95° C. for 10 min, followed by 92° C.; 30 sec, 60° C.; 30 sec, and 72° C.; 30 sec leading to a 334 bp amplicon. To assure the specificity of primers, some PCR products were cloned into pGEM-T easy vector (Promega, Madison, Wis., USA) and subjected to sequencing. RT-QPCR was performed as described.[6] cDNA samples were used as template and β-actin (endogenous housekeeping gene) was quantified as a positive control against which the different template values were normalized.

Production of PRELP Protein

For expression in yeast, cDNA from PBMC of CLL patients (n=10) were pooled and a full-length PRELP transcript was PCR-amplified. The PCR product was cloned into pGEM-T easy vector and subcloned into pGAPZα-A vector for yeast *P. pastoris* (Invitrogen, Carlsbad, Calif., USA). The recombinant plasmids were selected for sequencing. After selecting an in-frame clone, the construct was linearized using AvrII restriction enzyme and transfected into *P. pastoris* strain SMD1168 (Invitrogen). The colonies were screened by gene specific PCR amplification and positive clones were selected for protein production. The supernatant of a 72 h cultured yeast clone was collected and concentrated up to 30 times using Amicon Ultra-15 Centrifugal Filter Units (Millipore Corporation, Bedford, Mass., USA).

For expression in mammalian cells, a full-length PRELP cDNA clone (transcript variant 1, SC111673, TrueClones, OriGene Technologies, Inc. Rockville, Md., USA) was subcloned into NotI site of a mammalian expression vector pCMV6-Neo (OriGene Technologies). After selection and sequencing of an in-frame clone, the plasmid was transfected into mouse SP2/0 cell line to obtain stable transfectants using jetPEI™ transfection reagent (Polyplus-transfection™, Illkirch, France). Cells were harvested, washed extensively and lysate prepared as described for Western blot.

Chemical Deglycosylation of PRELP Protein

Recombinant PRELP protein produced in yeast was subjected to chemical deglycosylation using trifluoromethanesulfonic acid (TFMS) (Sigma, St Louis, Mo., USA) and anisole (Fluka, Sigma). TFMS removes all carbohydrates chains from glycoproteins regardless of linkage and composition.[18]

250 µl of yeast culture supernatant was precipitated in 100% ethanol at −20° C. over night in two separate tubes. Protein pellets were collected by centrifugation at 15000 g for 20 min, washed in 95% ethanol, collected by centrifugation and air-dried for 1 h. 200 µl TFMS and anisole (9:1) was added to the dry pellets and the samples were incubated on ice for 2 and 4 h, respectively. The reaction was stopped by the addition of 2M Tris base (pH 8) until pH reached 6. The samples were dialysed against 10 mM phosphate buffer for 24 h, concentrated 20 times in Amicon Ultra-15 Centrifugal Filter Units (Millipore Corp.) and then subjected to Western blot.

Anti-PRELP Poly- and Monoclonal Antibodies

A rabbit anti-PRELP polyclonal antibody was produced against a 19-mer peptide (CGGKARAKGGFRLLQSVVI) purchased from Thermo Electron Corporation GmbH (Ulm, Germany) of which the 9 last amino acids correspond to the carboxy-terminal (C-terminal) part of human PRELP[9]. The antibody was purified by affinity chromatography.

Two mouse anti-PRELP monoclonal antibodies were produced using Keyhole limpet hemocyanin (KLH)-conjugated PRELP-peptides following a standard protocol with minor modifications.[19] One antibody was generated against the carboxy-terminal peptide (CGGKARAKGGFRLLQSVVI). The other was raised against the N-terminal region for which a 20-mer peptide (MRSPLCWLLPLLILASVAQG) (Thermo Electron) covering the whole signal sequence was used.

Western Blot

Cell lysates were prepared as described with minor modifications.[20] Briefly, $50 \times 10^6$ cells were lysed in 1 mL of buffer containing 0.2% triton-X, 130 mM HEPES, 4 mM $MgCl_2$, 10 mM EGTA with 2% proteinase inhibitor cocktail (Sigma). After 1 h incubation on ice, lysates were centrifuged at 2500 rpm for 5 min and the soluble fraction was collected ("upper phase"). The Triton-X resistant pellet was dissolved in 1× NuPAGE LDS Sample Buffer (Invitrogen) and sonicated for 3×15 sec ("lower phase"). The protein concentration was measured by Bio-Rad Protein Assay according to the manufacturer's instructions (Bio-Rad Laboratories, Hercules, Calif., USA). Cell lysate (20 µg), serum (dil 1:50), and yeast supernatants were subjected to Western blot using a 10% NuPAGE Bis-Tris gel (Invitrogen) at 120 V for 3 h under reducing conditions. Resolved proteins were transferred onto Immobilon-P PVDF membrane (Millipore Corp.) in a Mini-Transblot Cell (Invitrogen). The membranes were blocked at +4° C. over night with 5% non-fat milk (Semper, Stockholm, Sweden) in PBS plus 0.05% Tween 20 (PBS-T). Filters were incubated with 10 µg/ml of anti-PRELP rabbit polyclonal or mouse monoclonal antibody over night at +4° C. Following extensive washings in PBS-T, filters were incubated with a secondary horseradish peroxidise (HRP)-conjugated goat anti-rabbit or rabbit anti-mouse antibody (DakoCytomation, Glostrup, Denmark) for 1.5 h at room temperature. Filters were developed using Amersham Enhanced Chemiluminescence ECL™ system (GE Healthcare). To verify equal loading of samples, filters were stripped in a buffer containing 62.5 mM Tris-HCL, 2% SDS, 100 mM Mercaptoethanol (Sigma) at 50° C. for 30 min. Following 3×15 min washing in PBS-T, the membranes were re-probed with 2.5 µg/ml of a mouse anti-β-actin monoclonal antibody (Sigma).

Apoptosis Assay $2 \times 10^6$ target cells (CLL cells or PBMC of healthy donors) were incubated with 10 µg/ml of the Anti-PRELP mouse monoclonal antibodies, or relevant isotype controls in 1 ml of serum-free medium (CTL-010, Cellular Technology Ltd. OH, USA). After 18 hours of incubation at 37° C. in humidified air with 5% $CO_2$, cells were collected, washed twice with 1×PBS and resuspended in 100 ul of 1× binding buffer at a concentration of $1 \times 10^6$ cells/ml. 5 µl of FITC-conjugated Annexin V and PI (BD Biosciences) was added to the cells, vortexed and incubated at room temperature in the dark for 15 minutes. 100 µl of 1× binding buffer was added to the cells which then were analyzed by flow cytometry (FACSCalibur).

Experiments Performed During the Paris Convention Priority Year

Immunocytochemistry (ICC) and Immunohistochemistry (IHC)

For ICC the cell lines were cultured and harvested using 0.5% trypsin and 0.1% EDTA (Gibco) loaded $1-2 \times 10^4$ cells on 8 well laminated glass slide (Marienfeld, Germany) that homogenized in RPMI 1640 containing 20% FBS with subsequent incubation in moisturized conditions for overnight. After overnight incubation the medium was removed and the cells were washed with PBS for three times (3×3 min). Slides were dried at room temperature for 15 min, acetone-fixed (at −20° C.), permeabilized for 2 minutes and kept at 4° C. for 30 min until slides were dried. Slides washed with Tris-Buffered Saline, pH 7.4 containing 5% bovine serum albumin (TBS-BSA) three times (3×3 min). Slides were blocked with 5% sheep serum for 10 min at room temperature. The primary anti-PRELP antibodies were diluted with TBS-BSA to a final concentration of 5 µg/mL and incubated at room temperature for 60 minutes and then washed with TBS-BSA three times (3×3 min). Fluorescein isothiocyanate (FITC)-conjugated Sheep anti-mouse (ACECR, Tehran, Iran) was diluted with TBS-BSA in a ratio of 1:50 and incubated at room temperature for 45 minutes. Negative antibody control slides were incubated with mouse IgM (isotype control) at a final concentration of 10 µg/mL in TBS-BSA. After washing with TBS-BSA, the nuclei were counterstained by 4',6-diamidino-2-phenylindole dihydrochloride (DAPI) (Calbiochem, USA) at 1 µg/ml for 5 minutes, then the slides were washed, mounted in PBS-glycerol 80% and examined under a fluorescence microscope (Olympus, Tokyo, Japan).

For IHC the tissues upon receiving were stored at −80° C. At the time of performing the experiment, tissues were equilibrated at −20° C. for approximately 2 hour before attempting to sectioning.

Tissues were cut at 5 um thickness and allowed to air dry for 3-12 hour at room temperature. Tissue sections were fixed by immersing the slides in pre-cooled acetone (−20° C.) for 1.5 minute at (−20° C.) following 0.5 minute at 4° C.

The fixative were poured off and allowed acetone to be evaporated from the tissue sections for >20 minutes at 4° C. The sections were air-dried on bench for 5 minutes. Slides were rinsed in 300 ul TBS (PH=7.4)+0.1% BSA (TBS-BSA) for 3 minutes. The slides were covered by blocking reagent for 10 min at room temperature (5% non-Immune serum from secondary antibody species in TBS-BSA). Blocking solution was removed and 100 µl diluted antibody (Diluted antibody in TBS-BSA). Primary antibody was added to each section. Incubated at room temperature for one hour. After that the primary antibody was removed and slides were then washed with 200 ul TBS-BSA for 3 times (each 3 min)

100 ul of secondary sheep anti-mouse antibody (conjugated with FITC), diluted in TBS-BSA was added. Slides were incubated for 45 minute in the dark at room temperature. After that secondary antibody was removed and slides were washed with 200 ul TBS-BSA for 3 times (each 3 min).

100 µA of DAPI (0.1 µg/ml diluted in TBS-BSA) was added to each section. Slides were incubated approximately 5 minute in the dark at room temperature. After removing DAPI slides were then washed in 200 ul TBS-BSA 3 time (each 1 min). Coverslip was mounted using TBS-glycerol (50% v/v).

Flow Cytometry Analysis

Cells were harvested by 0.5% trypsin and 0.1% EDTA (Gibco) and washed thoroughly with PBS. According to the related protocol, sample analysis and data acquisition were performed by Flomax flow cytometry analysis software (Partec, Germany).

Results

PRELP Gene Expression

The expression of PRELP mRNA in leukemic cells from peripheral blood of CLL patients as well as of other hematological malignancies and healthy control donors was tested by RT-PCR. PBMC from all CLL patients (n=30) expressed PRELP (Table 3), irrespective of clinical phase (non-progressive/progressive). PRELP was also expressed in tumor cells of MCL patients (3/5) but not in AML (0/5), FL (0/2) T- or B-PLL (0/5), HCL (0/2), MM (0/6), CML (0/5), and ALL (0/10). PRELP was not expressed in fresh PBMC (lymphocytes and monocytes) of healthy donors (0/10), enriched normal blood B cells (0/6), T cells (0/4), or granulocytes (0/5).

PRELP was expressed in four CLL cell lines (EHEB, 183-E95, 232-B4, WAC3-CD5) but not in cell lines derived from myeloma (0/1), T cell leukemia (0/1), ALL (0/4), AML (0/1), CML (0/1), and NK cell lymphoma (0/1) (Table 4). Sequencing of cDNA from 10 CLL patients revealed no major mutations in the PRELP gene (data not shown).

Specificity of Anti-PRELP Antibodies

The MW of normal PRELP protein is 55 kDa[9]. The specificity of our anti-PRELP poly- and monoclonal antibodies was tested against recombinant PRELP expressed in SP2/0 mouse cell line (FIGS. 1A-C). Cells transfected with pCMV6-Neo vector alone were used as a negative control. In Western blot, the C-terminal polyclonal antibody recognized a major band of 55-58 kDa, corresponding to mature, glycosylated PRELP protein.[9] In addition, this polyclonal antibody detected three bands of 38 kDa, 44 kDa, and 48 kDa, presumably representing unglycosylated or partly glycosylated PRELP.[10] The monoclonal antibodies against the C-terminal as well as the N-terminal, recognized only the 38 kDa PRELP. This may be due to that the monoclonal antibodies might recognize epitopes that are hidden by secondary structures in the mature PRELP protein.

PRELP Protein Expression

Figure 2:
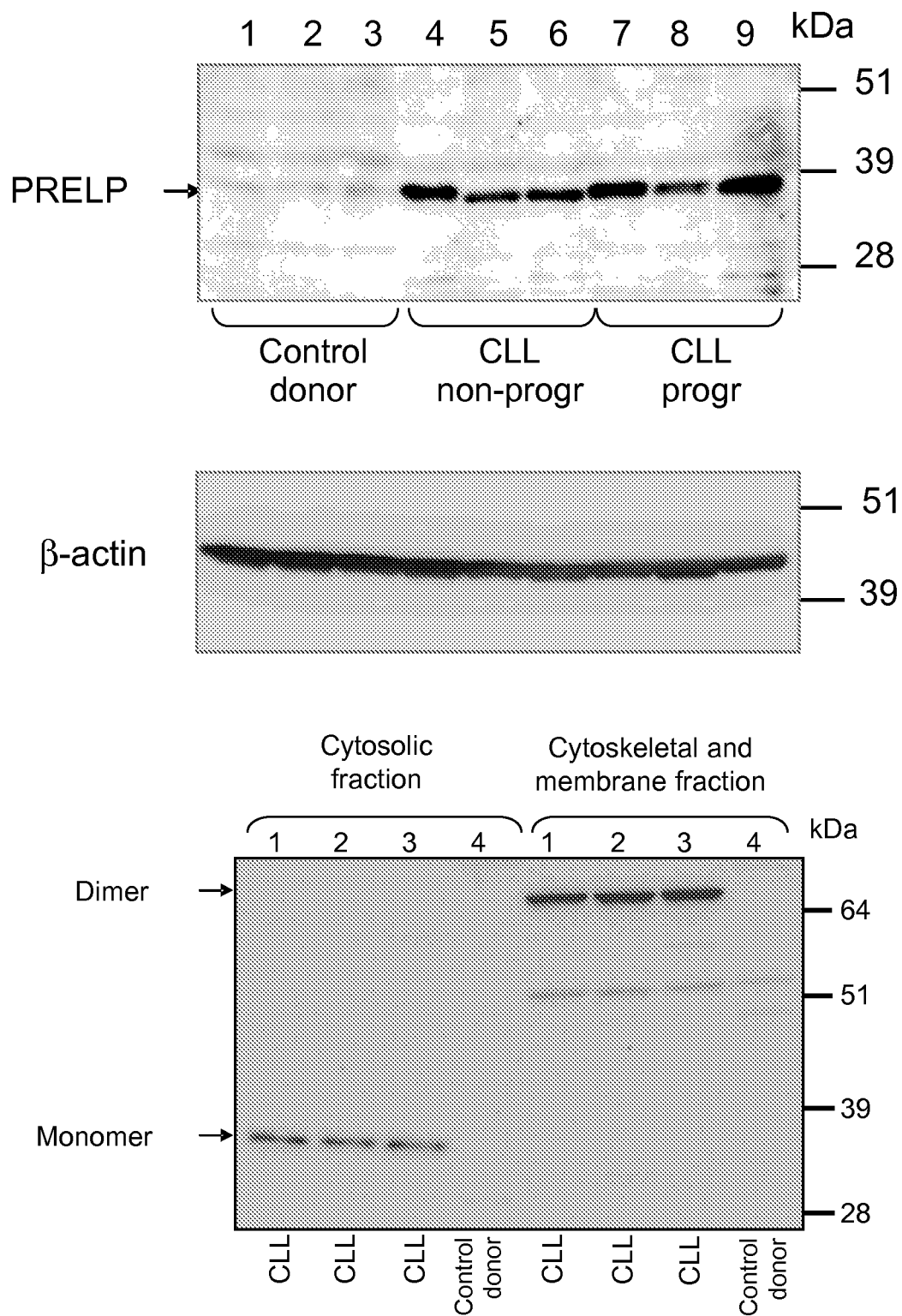
FIG. 2. Western blot of cell lysates from CLL patients and healthy control donors. A) Cytosolic cell fraction from three healthy controls, three non-progressive CLL and three progressive CLL patients. Upper panel: a rabbit anti-C-terminal PRELP polyclonal antibody detecting a 38 kDa band in CLL cells but not in healthy donor PBMC. Lower panel: The same membrane stripped and re-probed with an anti-β-actin monoclonal antibody. B) Cytosolic and cytoskeletal/membrane fractions respectively of three CLL patients and one healthy donor. The N-terminal monoclonal anti-PRELP antibody recognized 38 kDa monomer PRELP in the cytosolic fraction and a 76 kDa band probably representing a dimer of PRELP in the cytoskeletal and membrane fraction.
Figure 3:
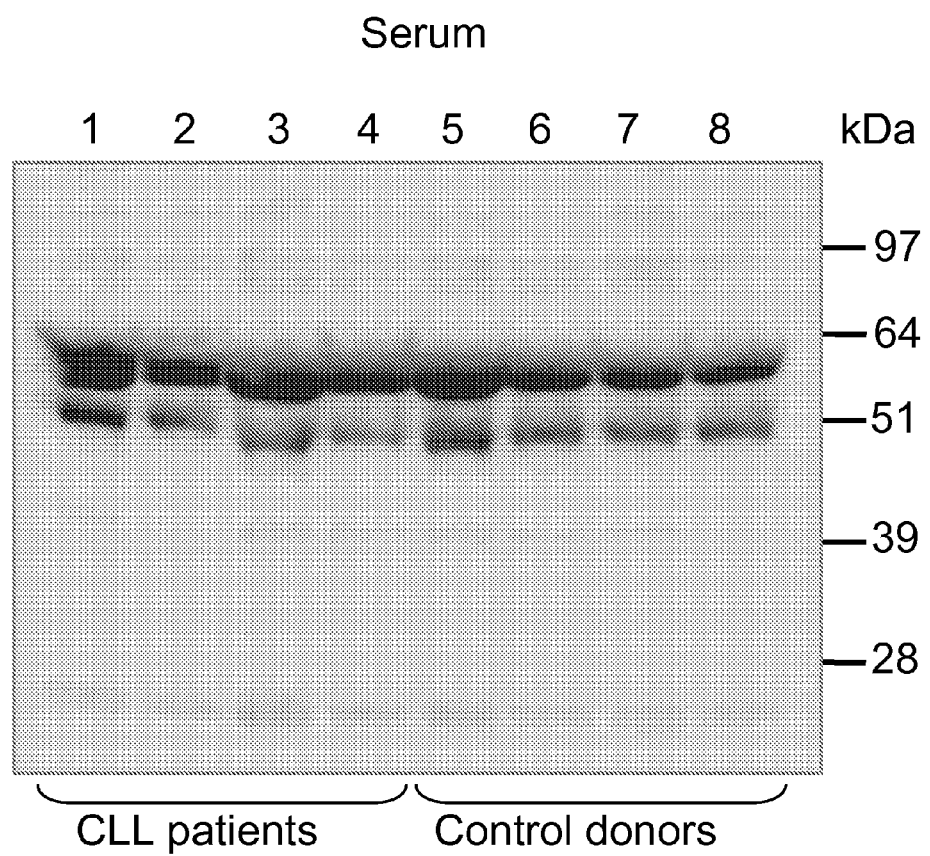
FIG. 3. Western blot of serum samples (1:50) from CLL patients (n=4) and healthy donors (n=4). A rabbit anti-C-terminal PRELP polyclonal antibody detected 50 kDa and 58 kDa PRELP bands in all samples.

PBMC from CLL patients (n=30) were tested for PRELP protein expression in Western blot. Tumor cell lysates were prepared by a 2-step method giving rise to two fractions. In the upper fraction, representing the cytosolic part, a band of 38 kDa was detected in all CLL patients (FIG. 2A). In the Triton-X resistant lower fraction considered to contain membrane and cytoskeletal structures[20] a band of approximately 76 kDa was seen (FIG. 2B). The 38 kDa band was recognized both by the C-terminal (monoclonal and polyclonal) and the N-terminal (monoclonal) antibodies eliminating the possibility that the 38 kDa fragment was a degradation product. The 76 kDa band was detected only by the monoclonal N-terminal antibody. A plausible explanation is that the 76 kDa variant had the signal peptide uncleaved and the C-terminal part hidden, which might be due to dimer formation. All four CLL lines also expressed the 38 kDa PRELP as well as the 76 kDa dimer (data not shown). PBMC of healthy control donors (n=10) did not express any PRELP protein variants (FIG. 2A-B). We also analyzed serum from 8 CLL patients and 8 healthy control donors by Western blot. All serum samples showed two bands, 50 and 58 kDa, representing mature glycosylated PRELP[10] (FIG. 3). The 38 kDa and 76 kDa PRELP proteins were not detected in serum from either patients or normal donors.

Deglycosylation of the PRELP Protein

Figure 4:
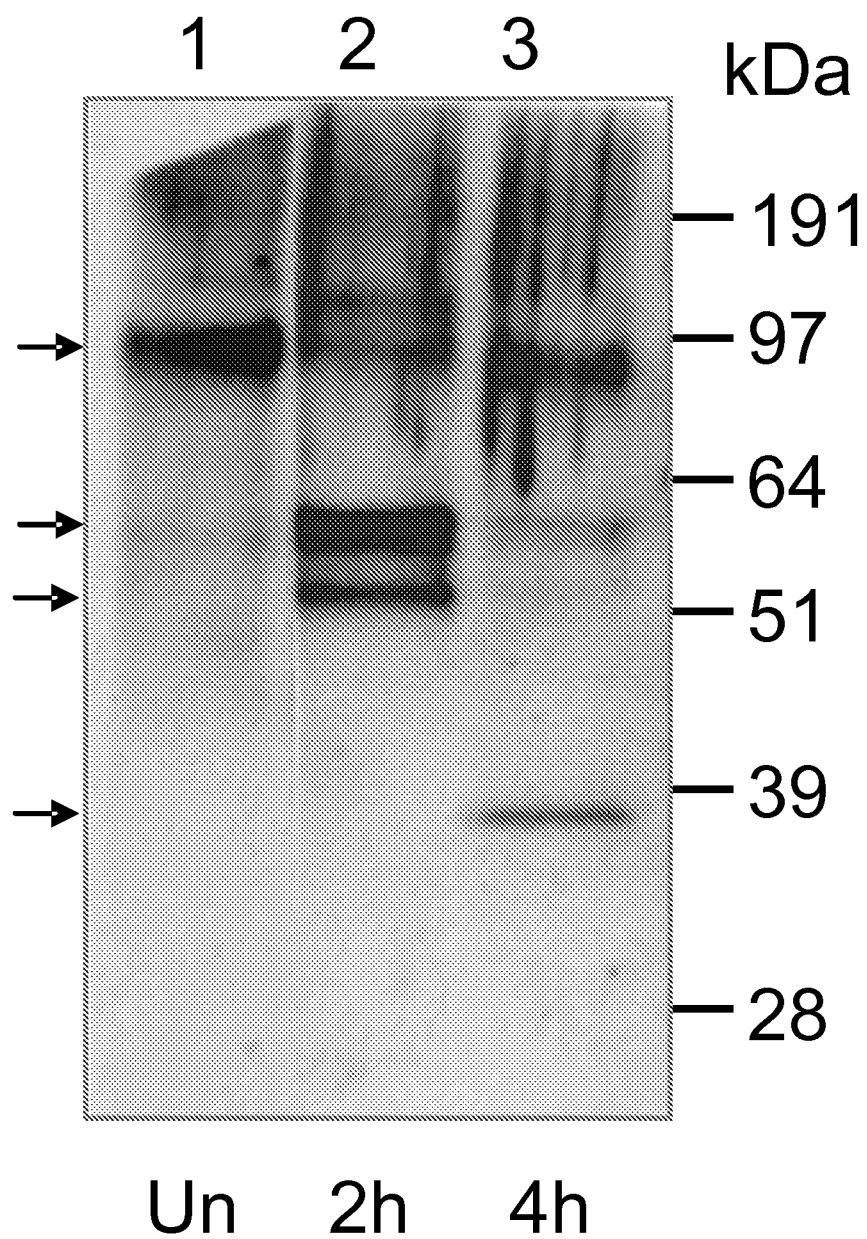
FIG. 4. Chemical deglycosylation of recombinant PRELP produced in yeast, mature PRELP devoided of the signal peptide. Western blot was performed using an anti-C-terminal polyclonal antibody. Lane 1: Untreated yeast-derived recombinant PRELP, Lanes 2 and 3: Yeast-derived recombinant PRELP treated with TFMS for 2 and 4 h, respectively. After complete removal of the carbohydrate structures, a 38 kDa band appeared.

Untreated yeast-derived PRELP had a MW of about 100 kDa (FIG. 4) which may represent a dimer of the mature glycosylated PRELP (55 kDa). After chemical deglycosylation using TFMS for 2 h, bands in the region of 51-64 kDa appeared, which may represent monomers of the mature glycosylated PRELP. After TFMS treatment for 4 h, a band of 38 kDa was seen, corresponding to completely deglycosylated PRELP protein (FIG. 4).

Apoptosis Assay

Figure 5:
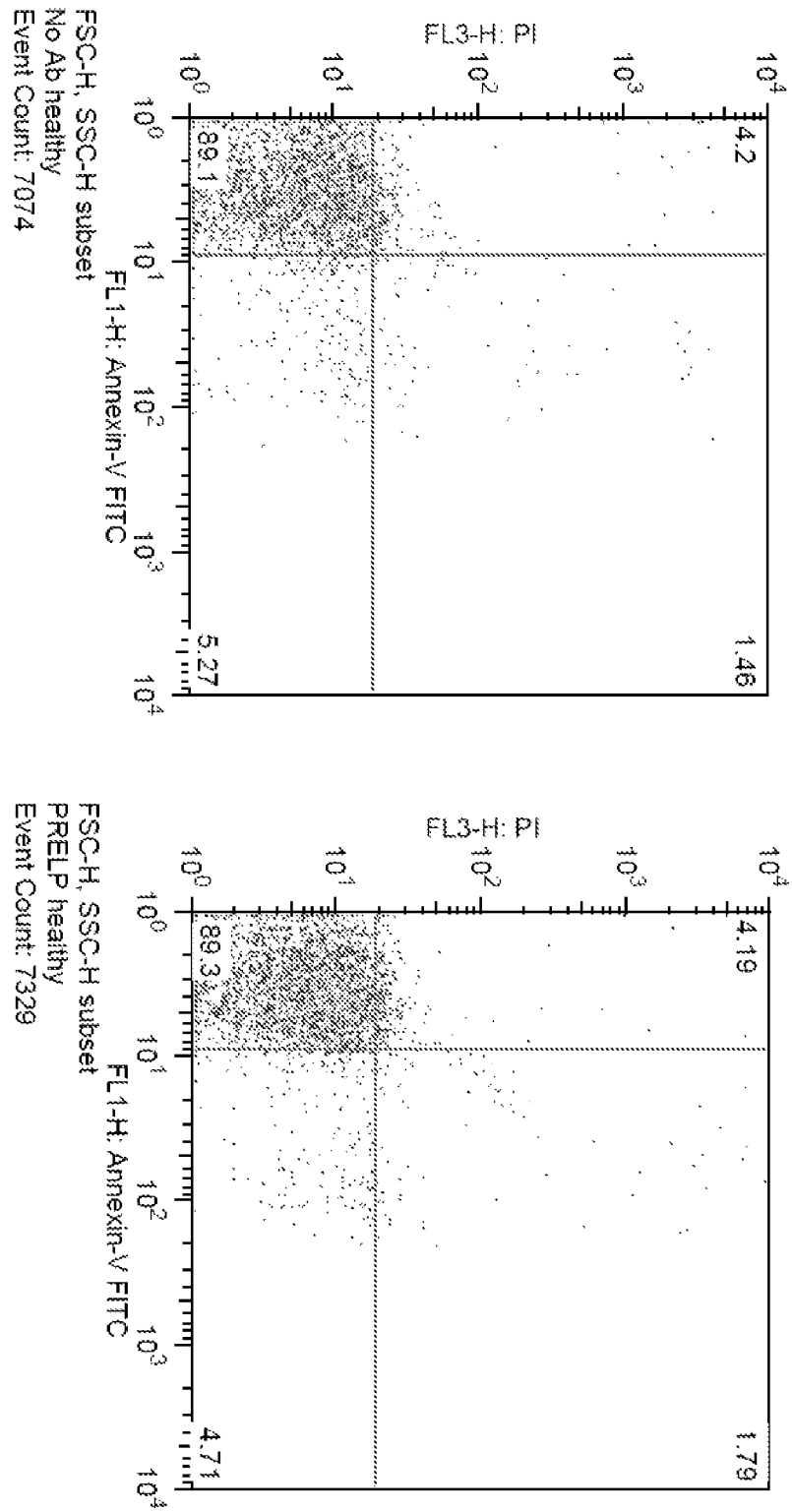
FIG. 5. Apoptosis was assayed with Annexin V-FITC and propidium iodide (PI) staining. Healthy PBMC were incubated in the presence or absence of anti-PRELP antibody for 18 hrs. A) Dot plots diagram representing healthy control with no antibody (No Ab). B) 10 ug of anti-PRELP antibody (PRELP-SS Clone 6G1-G11) on PBMC from a healthy individual. No apoptotic effect was observed in healthy PBMC with and without antibody.
Figure 6:
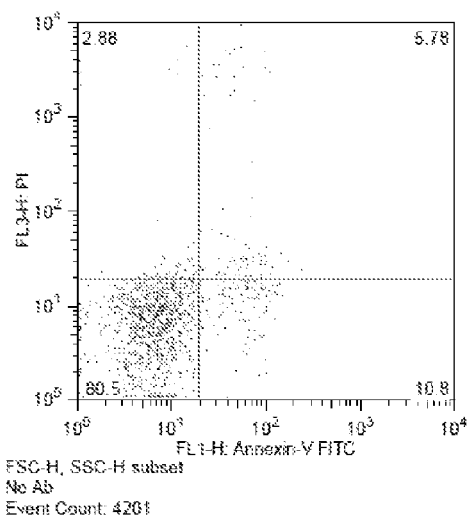
FIG. 6. Apoptosis was assayed with Annexin V-FITC and propidium iodide (PI) staining. CLL cells were incubated in the presence or absence of anti-PRELP antibody for 18 hrs. A) Dot plots diagram representing a CLL patient with no antibody (No Ab) with 10.8% spontaneous apoptosis. B, C, D) 2.5, 5, and 7.5 ug of anti-PRELP antibody (PRELP-SS Clone 6G1-G11) were incubated with equal number of leukemic cells, respectively. The results show dose-dependent effect of apoptosis on CLL cells. The apoptosis was increased from 10.8 to 16.9, 32.2, and 39.2% respective to 2.5, 5, and 7.5 ug of the antibody.
Figure 6:
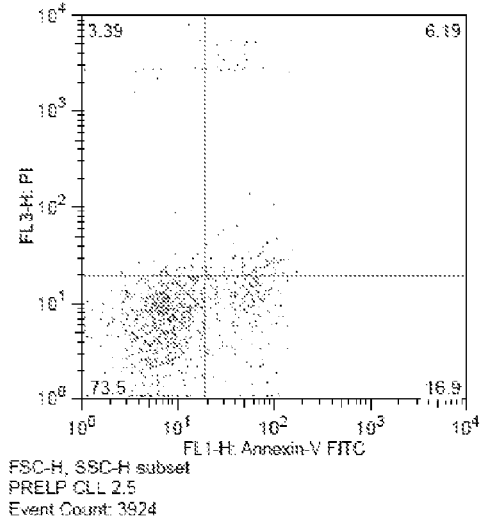
Figure 6:
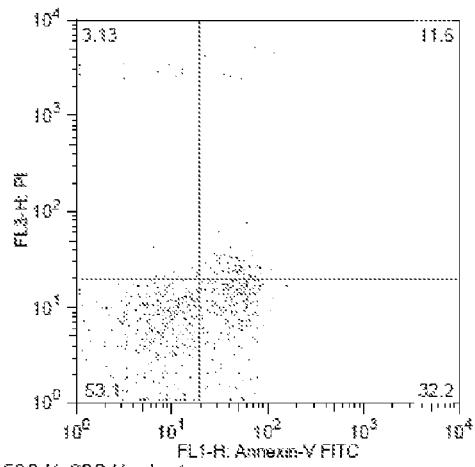
Figure 6:
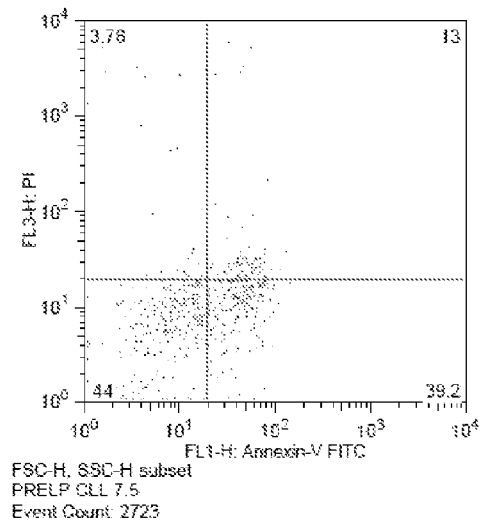

The results of the apoptosis assay are presented in FIGS. 5 and 6.

Results of Experiments Performed During the Paris Convention Priority Year

Figure 7:
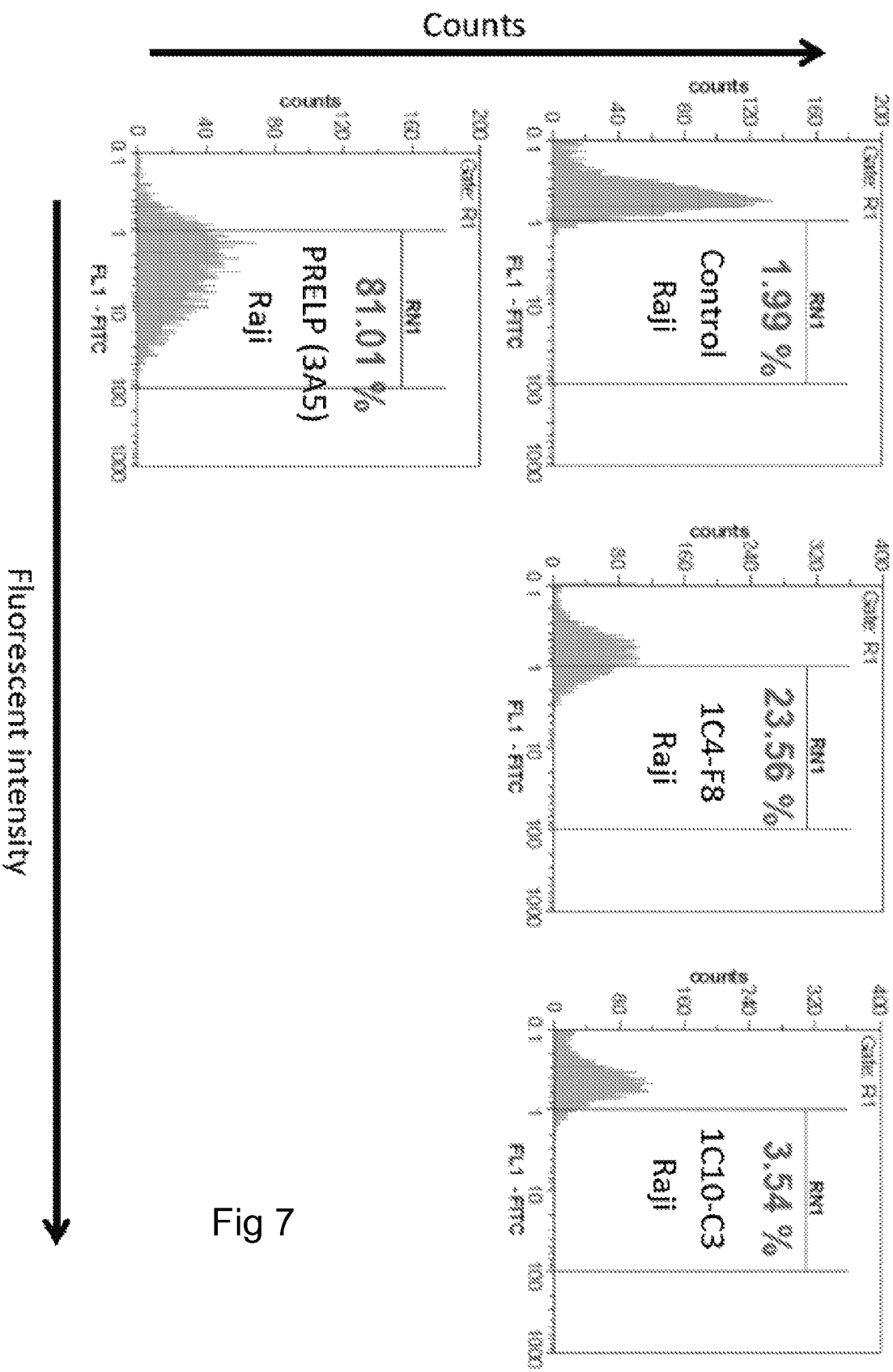
FIG. 7. Cell surface staining of human Human B cell lymphoma cell lines using three clones of anti-PRELP monoclonal antibodies of 1C4-F8, 1C10-C3, and 3A5 generated against N-terminal part of human PRELP. The mouse IgM was used as isotype control and sheep anti-mouse Ig FITC-conjugated was used as secondary antibody.
Figure 8A:
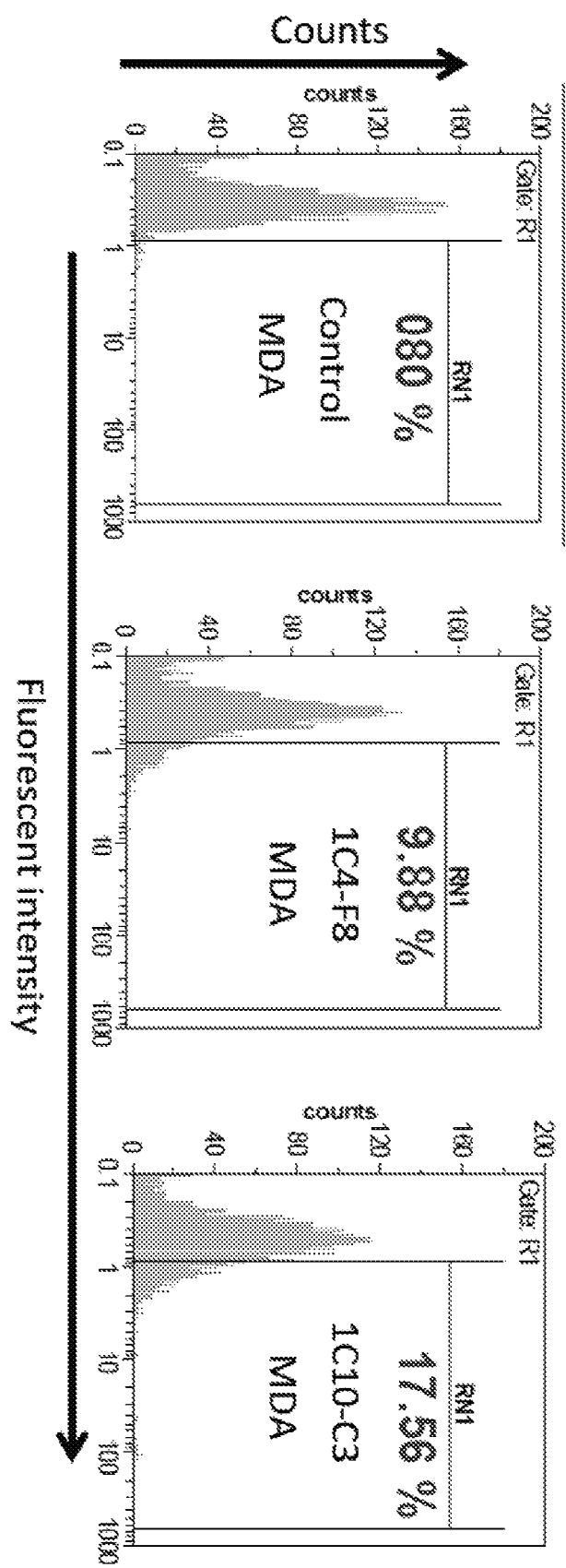
FIG. 8. A) Cell line MDA (Human breast cancer). B) Cell line 2780S (Human ovarian carcinoma) and 2008C13R (Human ovarian carcinoma). C) Cell line caov4 (Human ovarian carcinoma). The mouse IgM was used as isotype control and sheep anti-mouse Ig FITC-conjugated was used as secondary antibody.
Figure 8B:
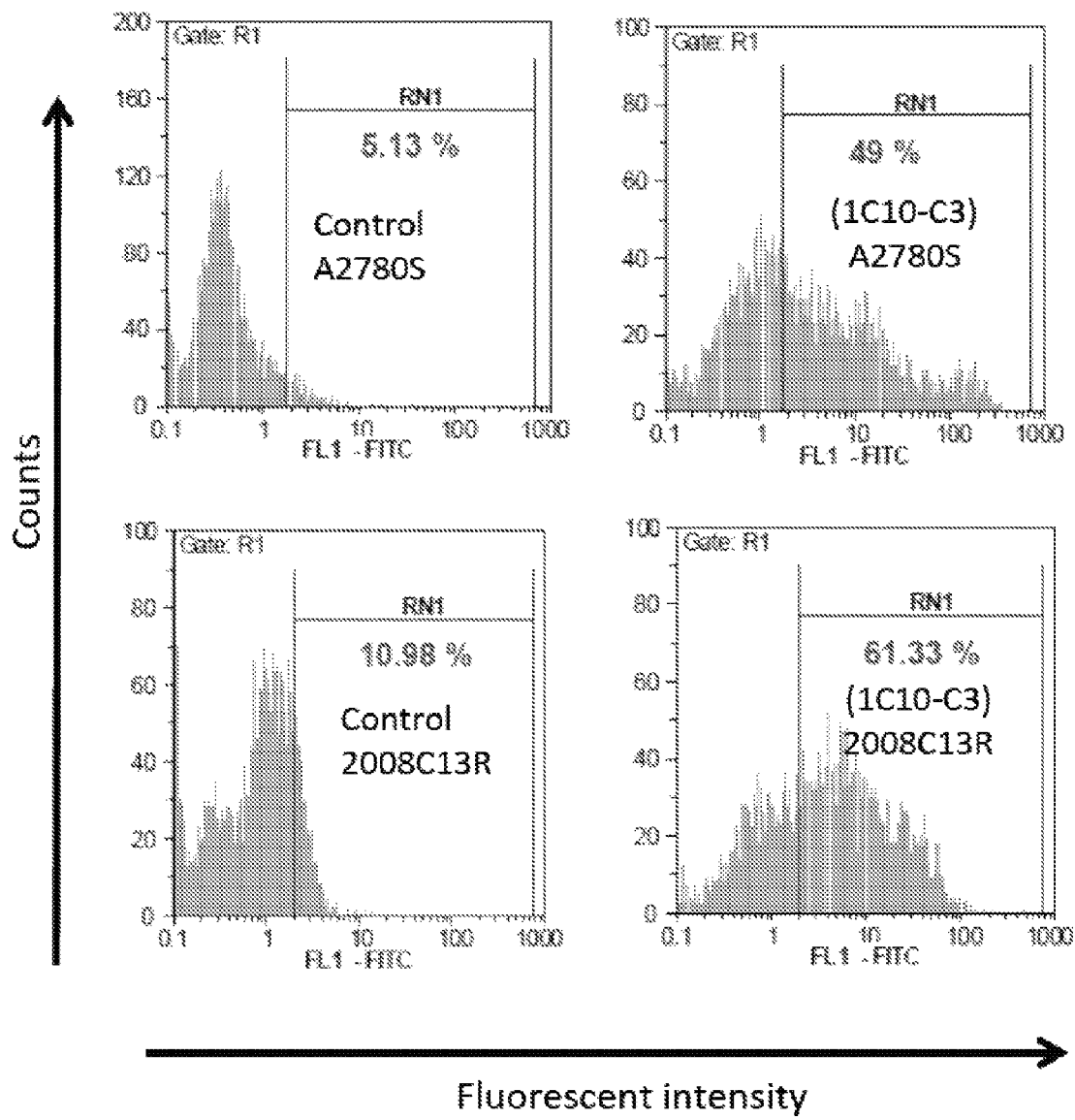
Figure 8C:
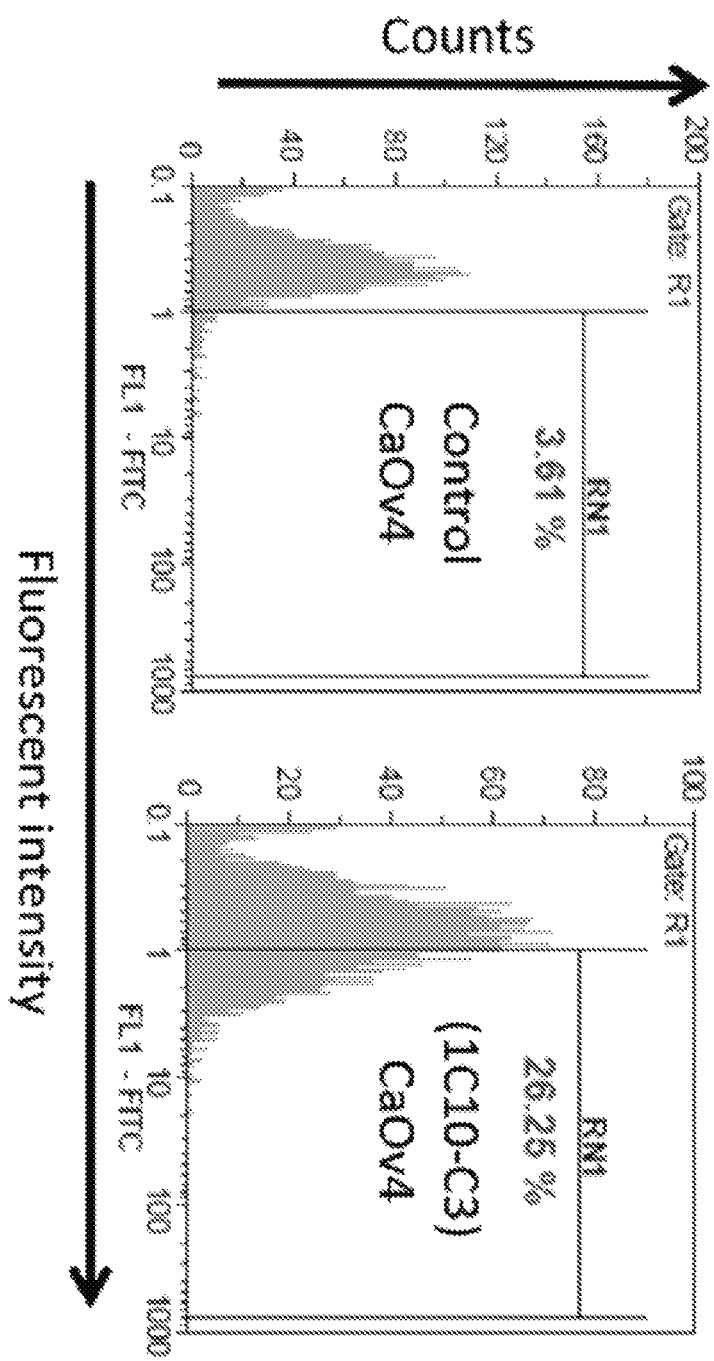

The expression of PRELP was studied in two cell lines including Raji (human B cell lymphoma) and 183-E95 (chronic lymphocytic leukemia line) by cell surface staining (flow cytometry). Flow cytometry experiments using different clones of anti-PRELP antibodies showed a reactivity of 22-80% on Raji in which the clone 3A5 showing highest reactivity (FIG. 7). The expression of PRELP was studied in one human breast cancer cell line MDA showing 9-17% reactivity by flow cytometry depending on the clonality of anti-PRELP antibody (FIG. 8A). Expression profile of PRELP in three ovarian carcinoma cell lines A2780S, 2008C13R, and CaOv4 was 44, 50, and 23%, respectively by flow cytometry using anti-PRELP antibody clone 1C10-C3 (FIGS. 8B and 8C).

Figure 9A:
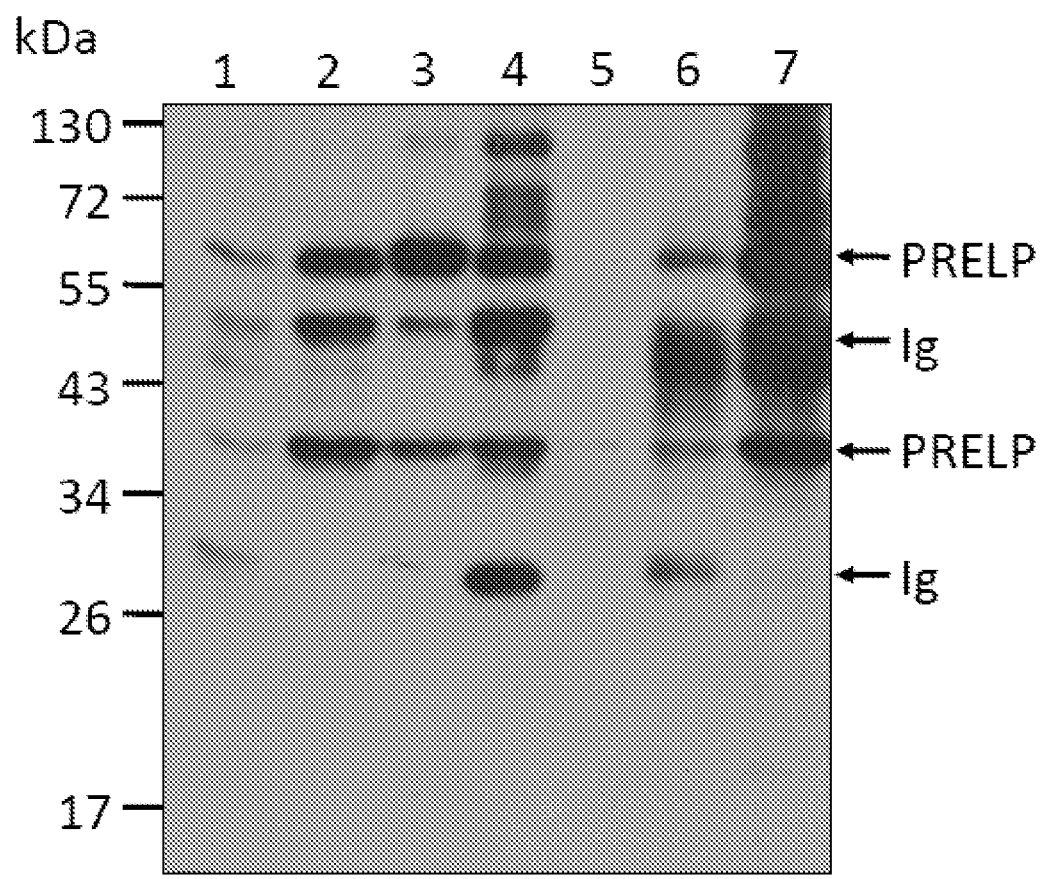
FIG. 9. Western blot analysis of different tissues and cell lines using two clones of anti-PRELP monoclonal antibodies of 4A4 and 1C10-C3 generated against N-terminal part of human PRELP both at reducing and non-reducing conditions. The HRP-conjugated sheep anti-mouse Ig was used as secondary antibody. A) Reducing conditions: Lane 1. Tumor cell lysate from a 23 year-old female patient with Neuroblastoma, Lane 2. Tumor cell lysate from abdominal mass of a 35 month-old female patient with Neuroblastoma, Lane 3. Tumor cell lysate from abdominal mass of a 34 month-old female patient with Neuroblastoma, Lane 4. Tumor cell lysate from brain mass of a 25 month-old female patient with medullablastoma, Lane 5. Cell lysate of U373 cell line (human glioblastoma), Lane 6. Cell lysates from a healthy human skin, lane 7. Cell lysate of PBMC from a CLL patient. Anti-PRELP clone 4A4 used as primary antibody.

Tumor tissues from three patients with neuroblastoma and one patient with medullablastoma also showed expression of PRELP using anti-PRELP antibody clone 4A4 (FIG. 9A). The expression of PRELP was higher in tumor tissues in comparison to PBMC from a healthy donor (FIG. 9A).

Figure 9B:
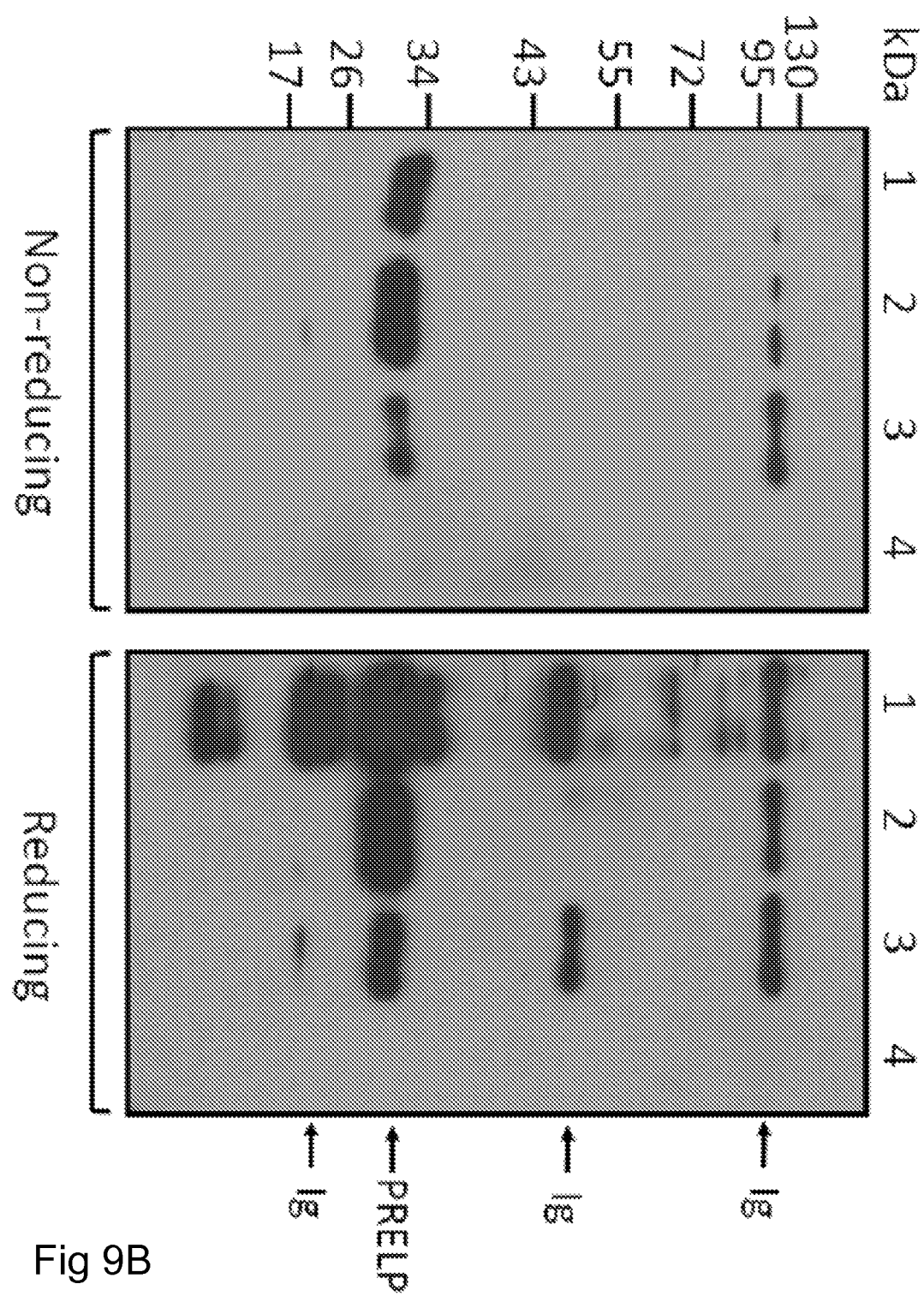

Western blot analysis of lysates from cell lines MDA (human breast cancer), U373 (Human glioblastoma), and PC3 (Human prostate cancer) showed strong expression of PRELP with no reactivity with human PBMC from a healthy donor (FIG. 9B).

Immunocytochemistry (ICC) on human breast cancer cell line SKBR3 showed a strong expression of PRELP using anti-PRELP antibody clone 1C10-C3 (FIG. 10). No expression of PRELP was detected in normal human tissues of breast, skin, and testis (FIGS. 11-13).

Table 5 shows a summary of PRELP expression in different tissues and cell lines both in pathological and non-pathological samples using both N-terminal and C-terminal anti-PRELP antibodies.

TABLE 1

Clinical characteristics of CLL patients (n = 30)

| Characteristic | Frequency % |
|---|---|
| Sex | |
| Male | 72 |
| Female | 28 |
| Age, years | |
| 40-49 | 7 |
| 50-59 | 7 |
| 60-69 | 36 |
| 70-79 | 40 |
| 80-89 | 10 |
| Clinical phase | |
| Progressive * | 47 |
| Non-progressive * | 53 |
| Rai Stage | |
| 0 | 36 |
| I | 27 |
| II | 7 |
| III | 27 |
| IV | 3 |
| Treatment | |
| Treated ** | 33 |
| Untreated | 67 |

\* for definition, see materials and methods (patients and controls)
\*\* standard treatments including chlorambucil, fludarabine, cyclophosphamide

TABLE 2

Primers and probes used in PCR amplification and quantifications of PRELP

| Target | Primer (5'→3') | Position | Amplicon size (bp) | Reference |
|---|---|---|---|---|
| PRELP | (SEQ ID NO: 9) S: TCAAGAACCTCATGCAGCTCAA | 777-798 | 334 | g.b. |
| (RT-PCR) | (SEQ ID NO: 10) AS: ATCTGGGTTCCGTTGATTTTCTC | 1088-1110 | | NM_002725 |
| β-actin | (SEQ ID NO: 11) S: ATTAAGGAGAAGCTGTGCTACGTC | 707-730 | 215 | g.b. |
| (RT-PCR) | (SEQ ID NO: 12) AS: ATGATGGAGTTGAAGGTAGTTTCG | 898-921 | | NM_001101 |
| PRELP | (SEQ ID NO: 13) S: TGCCTTCATTCGGCTTAACT | 922-941 | 189 | g.b. |
| (RT- | (SEQ ID NO: 14) AS: ATCTGGGTTCCGTTGATTTTCTC | 1088-1110 | | NM_002725 |

TABLE 2-continued

Primers and probes used in PCR amplification and quantifications of PRELP

| Target | Primer (5'→3') | Position | Amplicon size (bp) | Reference |
|---|---|---|---|---|
| QPCR) | (SEQ ID NO: 15) Probe: QTCCACCTGTCCCACAACAGGATCA9 | 1005-1028 | | |
| β-actin (RT-QPCR) | (SEQ ID NO: 16) S: CGACAGGATGCAGAAGGAGA | 929-948 | 161 | g.b. |
| | (SEQ ID NO: 17) AS: CGTCATACTCCTGCTTGCTG | 1070-1089 | | NM_001101 |
| | (SEQ ID NO: 18) Probe: QAAGATCAAGATCATTGCTCCTCCTGAG9 | 975-1001 | | |

S = Sense,
AS = Antisense,
Q = Blue-6-FAM,
9 = TAMRA,
g.b = genebank

TABLE 3

PRELP gene expression (RT-PCR) of freshly isolated tumor cells of patients with various hematological malignancies and blood PBMC of healthy control donors

| Cell source | No. of positive cases/total no. |
|---|---|
| Chronic lymphocytic leukemia (PBMC) | 30/30 |
| Mantle cell lymphoma (PBMC) | 3/5 |
| Chronic myelogenous leukemia (PBMC) | 0/5 |
| Acute lymphoblastic leukemia (PBMC) | 0/10 |
| Acute myelogenous leukemia (PBMC) | 0/5 |
| Prolymphocytic leukemia (B and T cell types) (PBMC) | 0/5 |
| Hairy cell leukemia (PBMC) | 0/2 |
| Follicular lymphoma (BMMC) | 0/2 |
| Multiple myeloma (BMMC) | 0/6 |
| Normal healthy PBMC (lymphocytes and monocytes) | 0/10 |
| Normal blood T cells** | 0/4 |
| Normal blood B cells* | 0/6 |
| Normal blood granulocytes** | 0/5 |

PBMC; peripheral blood mononuclear cells, BMMC; bone marrow mononuclear cells
*Purity > 90%,
**purity > 98%

TABLE 4

PRELP gene expression (RT-PCR) in hematological cell lines

| Malignancy | Cell line | |
|---|---|---|
| CLL | EHEB | Positive |
| CLL | I83-E95 | Positive |
| CLL | 232-B4 | Positive |
| CLL | WAC3-CD5 | Positive |
| Multiple myeloma | LP-1 | Negative |
| T cell leukemia | SKW3 | Negative |
| Acute lymphoblastic leukemia | HUT-78 | Negative |
| Acute lymphoblastic leukemia | HPB-ALL | Negative |
| Acute lymphoblastic leukemia | MOLT-4 | Negative |
| Acute lymphoblastic leukemia | JURKAT | Negative |
| Promyelocytic leukemia | HL60 | Negative |
| Chronic myelogenous leukemia | K562 | Negative |
| NK lymphoma | YT | Negative |

TABLE 5

Expression profile of PRELP in different pathological and non-pathological human cells and tissues using different anti-PRELP monoclonal antibodies in different read-out systems

| Cell line/tissue | Description | W.B | FACS | IHC/ICC | Summary |
|---|---|---|---|---|---|
| SKBR3 | Human breast cancer | ND | ND | Positive | + |
| MDA | Human breast cancer | Positive | 9-17% | ND | + |
| BT474 | Human breast cancer | ND | 65% | ND | + |
| 2008C13R | Human ovarian cancer | ND | 44% | ND | + |
| A2087S | Human ovarian cancer | ND | 50% | ND | + |
| CaOv4 | Human ovarian cancer | ND | 25% | ND | + |
| PC3 | Human prostate cancer | Positive | ND | ND | + |
| U373 | Human Glioblastoma | Positive | ND | ND | + |
| Raji | Human Burkitt's lymphoma | ND | 22-80% | ND | + |
| Breast | Human normal breast tissue | ND | ND | Negative | − |
| Skin | Human normal skin tissue | ND | ND | Negative | − |
| Testis | Human normal testis tissue | ND | ND | Negative | − |
| PBMC-1 | Human normal PBMC-1 | Negative | 1-3% | ND | − |
| PBMC-2 | Human normal PBMC-2 | Negative | 1-3% | ND | − |
| PBMC-3 | Human normal PBMC-3 | Negative | 1-3% | ND | − |
| PBMC-4 | Human normal PBMC-4 | Negative | 1-3% | ND | − |

ND; not determined, FACS; flow cytometry, W-B; western blot, IHC; Immunohistochemistry, ICC; Immunocytochemistry

REFERENCES

1. Ghia P, Circosta P, Scielzo C, et al. Differential effects on CLL cell survival exerted by different microenvironmental elements. Curr Top Microbiol Immunol. 2005; 294:135-145.

2. Munk Pedersen I, Reed J. Microenvironmental interactions and survival of CLL B-cells. Leuk Lymphoma. 2004; 45:2365-2372.

3. Burger J A, Kipps T J. Chemokine receptors and stromal cells in the homing and homeostasis of chronic lymphocytic leukemia B cells. Leuk Lymphoma. 2002; 43:461-466.
4. Caligaris-Cappio F. Biology of chronic lymphocytic leukemia. Rev Clin Exp Hematol. 2000; 4:5-21.
5. Klein U, Tu Y, Stolovitzky G A, et al. Gene expression profiling of B cell chronic lymphocytic leukemia reveals a homogeneous phenotype related to memory B cells. J Exp Med. 2001; 194:1625-1638.
6. Mikaelsson E, Danesh-Manesh A H, Luppert A, et al. Fibromodulin, an extracellular matrix protein: characterization of its unique gene and protein expression in B-cell chronic lymphocytic leukemia and mantle cell lymphoma. Blood. 2005; 105:4828-4835.
7. Abba M C, Fabris V T, Hu Y, et al. Identification of novel amplification gene targets in mouse and human breast cancer at a syntenic cluster mapping to mouse ch8A1 and human ch13q34. Cancer Res. 2007; 67:4104-4112.
8. Sztrolovics R, Chen X N, Grover J, Roughley P J, Korenberg J R. Localization of the human fibromodulin gene (FMOD) to chromosome 1q32 and completion of the cDNA sequence. Genomics. 1994; 23:715-717.
9. Grover J, Chen X N, Korenberg J R, Recklies A D, Roughley P J. The gene organization, chromosome location, and expression of a 55-kDa matrix protein (PRELP) of human articular cartilage. Genomics. 1996; 38:109-117.
10. Bengtsson E, Neame P J, Heinegard D, Sommarin Y. The primary structure of a basic leucine-rich repeat protein, PRELP, found in connective tissues. J Biol. Chem. 1995; 270:25639-25644.
11. Bengtsson E, Aspberg A, Heinegard D, Sommarin Y, Spillmann D. The amino-terminal part of PRELP binds to heparin and heparan sulfate. J Biol. Chem. 2000; 275: 40695-40702.
12. Bengtsson E, Morgelin M, Sasaki T, Timpl R, Heinegard D, Aspberg A. The leucine-rich repeat protein PRELP binds perlecan and collagens and may function as a basement membrane anchor. J Biol. Chem. 2002; 277:15061-15068.
13. Daneshmanesh A H, Mikaelsson E, Jeddi-Tehrani M, et al. Rorl, a cell surface receptor tyrosine kinase is expressed in chronic lymphocytic leukemia and may serve as a putative target for therapy. Int J. Cancer. 2008; 123:1190-1195.
14. Harris N L, Jaffe E S, Diebold J, et al. The World Health Organization classification of neoplastic diseases of the haematopoietic and lymphoid tissues: Report of the Clinical Advisory Committee Meeting, Airlie House, Va., November 1997. Histopathology. 2000; 36:69-86.
15. Hallek M, Cheson B D, Catovsky D, et al. Guidelines for the diagnosis and treatment of chronic lymphocytic leukemia: a report from the International Workshop on Chronic Lymphocytic Leukemia updating the National Cancer Institute-Working Group 1996 guidelines. Blood. 2008; 111:5446-5456.
16. Wendel-Hansen V, Sallstrom J, De Campos-Lima P O, et al. Epstein-Barr virus (EBV) can immortalize B-cll cells activated by cytokines Leukemia. 1994; 8:476-484.
17. Rezvany M R, Jeddi-Tehrani M, Rabbani H, et al. Autologous T lymphocytes may specifically recognize leukaemic B cells in patients with chronic lymphocytic leukaemia. Br J. Haematol. 2000; 111:608-617.
18. Edge A S. Deglycosylation of glycoproteins with trifluoromethanesulphonic acid: elucidation of molecular structure and function. Biochem J. 2003; 376:339-350.
19. Kohler G, Milstein C. Continuous cultures of fused cells secreting antibody of predefined specificity. Nature. 1975; 256:495-497.
20. Ferreira A, Busciglio J, Caceres A. Microtubule formation and neurite growth in cerebellar macroneurons which develop in vitro: evidence for the involvement of the microtubule-associated proteins, MAP-1a, HMW-MAP2 and Tau. Brain Res Dev Brain Res. 1989; 49:215-228.
21. Vuillier F, Dumas G, Magnac C, et al. Lower levels of surface B-cell-receptor expression in chronic lymphocytic leukemia are associated with glycosylation and folding defects of the mu and CD79a chains. Blood. 2005; 105: 2933-2940.
22. Le Goff M M, Hindson V J, Jowitt T A, Scott P G, Bishop P N. Characterization of opticin and evidence of stable dimerization in solution. J Biol. Chem. 2003; 278:45280-45287.
23. Mansson B, Wenglen C, Morgelin M, Saxne T, Heinegard D. Association of chondroadherin with collagen type II. J Biol. Chem. 2001; 276:32883-32888.
24. Scott P G, Dodd C M, Bergmann E M, Sheehan J K, Bishop P N. Crystal structure of the biglycan dimer and evidence that dimerization is essential for folding and stability of class I small leucine-rich repeat proteoglycans. J Biol. Chem. 2006; 281:13324-13332.
25. Scott P G, McEwan P A, Dodd C M, Bergmann E M, Bishop P N, Bella J. Crystal structure of the dimeric protein core of decorin, the archetypal small leucine-rich repeat proteoglycan. Proc Natl Acad Sci USA. 2004; 101:15633-15638.
26. Grant D S, Yenisey C, Rose R W, Tootell M, Santra M, Iozzo R V. Decorin suppresses tumor cell-mediated angiogenesis. Oncogene. 2002; 21:4765-4777.
27. Yamaguchi Y, Ruoslahti E. Expression of human proteoglycan in Chinese hamster ovary cells inhibits cell proliferation. Nature. 1988; 336:244-246.
28. Yoshida K, Suzuki Y, Honda E, et al. Leucine-rich repeat region of decorin binds to filamin-A. Biochimie. 2002; 84:303-308.
29. Rufo A, Alamanou M, Rucci N, Capulli M, Heinegard D, Teti A. The matrix PROLINE/Arginine-Rich End Leucin-Rich Repeat Protein (PRELP) impairs osteoclastogenesis by inhibiting NF-kappa B activity. Bone. 2008; 42; 39-40 Abstract 52

The invention claimed is:

1. An isolated antibody, or fragment thereof, having the VH sequence SEQ ID NO: 1 or SEQ ID NO: 5 and/or VL sequence SEQ ID NO: 2.

2. An isolated antibody or fragment thereof, which is specific for the polypeptide sequence of MRSPLCWLLPLLI-LASVAQG (SEQ ID NO: 7) of the N-terminal part of the 38 kDA form of PRELP.

3. The antibody or a fragment thereof according to claim 2 which is bound to a detectable moiety.

4. The antibody or fragment thereof according to claim 2 wherein the antibody is a monoclonal antibody.

5. An antibody or fragment thereof according to any one of claims 1, 2 or 4, bound to a moiety having anti-cancer activity.

6. A composition comprising the antibody or a fragment thereof according to claim 1 and a carrier.

7. A composition comprising the antibody or fragment thereof comprising the antibody or a fragment thereof according to claim 2 and a carrier.

8. An in vitro method for assessing the risk that a subject suffers from chronic lymphocytic leukemia (CLL), comprising measuring the expression level of Proline/arginine-rich end leucine repeat protein (PRELP) in peripheral blood mononuclear cells isolated from said subject, by contacting the cells with an antibody or fragment thereof of any one of claims 1, 2 or 4 and measuring the expression level of PRELP, wherein an increased expression level of PRELP, as compared to healthy donors, indicates an increased probability of said subject suffering from CLL.

9. The method according to claim 8, wherein the expression level is measured as expression of a 38 kDa form of PRELP.

10. The method according to claim 8, wherein the expression level of unglycosylated PRELP is measured.

11. A method for treatment of chronic lymphocytic leukemia (CLL), comprising administering an antibody or fragment thereof of any one of claims 1, 2 or 4 to a subject suffering from CLL.

12. The method according to claim 11, wherein the antibody or fragment thereof is specific for an immunogen with the sequence MRSPLCWLLPLLILASVAQG (SEQ ID NO: 7), and wherein the antibody or fragment thereof bound to a moiety having anti-cancer activity.

13. A method for indicating a blood cell as a chronic lymphocytic leukemia (CLL) cell, comprising detecting a presence or non-presence of PRLEP on the surface of said blood cell by contacting the cell with an antibody or fragment thereof of any one of claims 1, 2 or 4, wherein the presence of PRELP on said surface of said cell indicates that said cell is a CLL.

14. The method according to claim 13, wherein the presence or non-presence of PRELP is measured as presence or non-presence of a 38 kDa form of PRELP.

15. The method according to claim 13, wherein the presence or non-presence of unglycosylated PRELP is measured.

* * * * *